US010954528B2

(12) United States Patent
Xie et al.

(10) Patent No.: US 10,954,528 B2
(45) **Date of Patent: *Mar. 23, 2021**

(54) SULFONYLUREA HERBICIDE RESISTANT TRANSGENIC PLANTS

(71) Applicant: BEIJING DABEINONG BIOTECHNOLOGY CO., LTD., Beijing (CN)

(72) Inventors: Xiangting Xie, Beijing (CN); Qing Tao, Beijing (CN); Xiaoming Bao, Beijing (CN)

(73) Assignee: BEIJING DABEINONG BIOTECHNOLOGY CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/086,298

(22) PCT Filed: Dec. 9, 2016

(86) PCT No.: PCT/CN2016/109176

§ 371 (c)(1),
(2) Date: Sep. 18, 2018

(87) PCT Pub. No.: WO2017/161921

PCT Pub. Date: Sep. 28, 2017

(65) Prior Publication Data

US 2019/0106705 A1 Apr. 11, 2019

(30) Foreign Application Priority Data

Mar. 22, 2016 (CN) .......................... 2016 1 0165121

(51) Int. Cl.

| | |
|---|---|
| ***C12N 15/82*** | (2006.01) |
| ***C12N 9/14*** | (2006.01) |
| ***C12N 5/10*** | (2006.01) |
| ***A01N 25/32*** | (2006.01) |
| ***A01N 47/36*** | (2006.01) |
| ***C07K 14/395*** | (2006.01) |

(52) U.S. Cl.

CPC ......... *C12N 15/8274* (2013.01); *A01N 25/32* (2013.01); *A01N 47/36* (2013.01); *C07K 14/395* (2013.01); *C12N 5/10* (2013.01); *C12N 9/14* (2013.01); *C12N 15/8275* (2013.01); *C12N 15/8278* (2013.01)

(58) Field of Classification Search

CPC .................................................. C12N 15/8274

See application file for complete search history.

(56) References Cited

U.S. PATENT DOCUMENTS 5,627,061 A * 5/1997 Barry ................. C12N 15/8275 435/320.1
6,064,754 A * 5/2000 Parekh ............ G01N 27/44704 382/129
9,062,284 B2 * 6/2015 Lira ..................... C12N 9/0004
9,669,247 B2 * 6/2017 Li ........................... A62D 3/02
2005/0112571 A1 * 5/2005 Gielen ........... C12Y 202/01006 435/6.12
2006/0130172 A1 * 6/2006 Whaley .................... C12N 9/88 800/278
2014/0325700 A1 * 10/2014 Li ............................ C12N 9/14 800/278
2019/0029252 A1 * 1/2019 Xie ........................ A01G 22/22
2019/0029257 A1 * 1/2019 Xie ........................ A01N 47/36
2019/0055576 A1 * 2/2019 Xie ......................... C12N 9/16

FOREIGN PATENT DOCUMENTS

| | | |
|---|---|---|
| CN | 102286501 | 12/2011 |
| CN | 105724139 | 7/2016 |
| CN | 105724140 | 7/2016 |
| CN | 105746255 | 7/2016 |
| CN | 105766992 | 7/2016 |
| CN | 105802933 | 7/2016 |
| WO | WO 2014090760 | 6/2014 |

OTHER PUBLICATIONS

Hang et al, Applied and Environmental Microbiology, Jan. 13, 2012, pp. 1962-1968. (Year: 2012).*
Green et al Pest Managment Science vol. 64, pp. 332-339 (Year: 2008).*
Hang, et al., "SulE, a Sulfonylurea Herbicide De-Esterification Esterase from Hansschlegelia zhihuaiae S113", Applied and Environmental Microbiology, 2012, 78(6): 1962-1968.
Hang, et al., "GenBank: JN617866.1", NCBI Database, 2012.
Hang, et al., "GenBank:AEX00103.1", NCBI Database, 2012.
Huang et al., "Isolation and characterization of a metsulfuron-methyl degrading bacterium *Methylopila* sp. S113", International Biodeterioration & Biodegradation, 2007, 60: 152-158.
Lu et al., "Study of Biochemical Pathway and Enzyme Involved in Metsulfuron-Methyl Degradation by *Ancylobacter* sp. XJ-412-1 Isolated from Soil", Curr Microbiol, 2011, 62: 1718-1725.
Yang et al., "Improved stability and enhanced efficiency to degradechlorimuron-ethyl by the entrapment of esterase SulE incross-linked poly (γ-glutamic acid)/gelatin hydrogel", Journal of Hazardous Materials, 2015, 287: 287-295.

* cited by examiner

*Primary Examiner* — David H Kruse
(74) *Attorney, Agent, or Firm* — James S. Keddie; Bozicevic, Field & Francis LLP

(57) ABSTRACT

A herbicide tolerant protein SUM1, a coding gene thereof and a use thereof, wherein the herbicide tolerant protein comprises: (a) a protein having an amino acid sequence as shown in SEQ ID NO: 1; or (b) a protein which is derived from (a) by substituting and/or deleting and/or adding one or more amino acids in the amino acid sequence of (a), and has the activity of thifensulfuron hydrolase. The herbicide tolerant protein SUM1 can show a higher tolerance to a plurality of sulfonylurea herbicides, can tolerate four-fold field concentration, and thus has a broad application prospect in plants.

20 Claims, 10 Drawing Sheets

Specification includes a Sequence Listing.

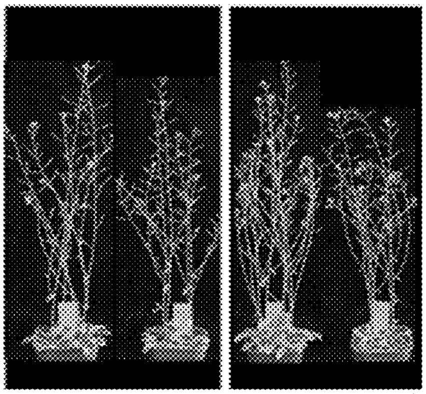

Arabidopsis thaliana(At)-Blank solvent
(Water)
Wild-type SUM1-01

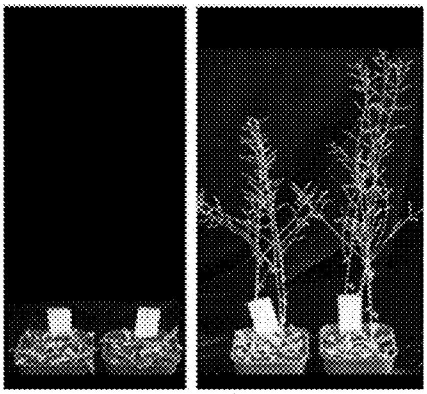

Arabidopsis thaliana(At)-1xTri.
(Tribenuron-methyl)
Wild-type SUM1-01

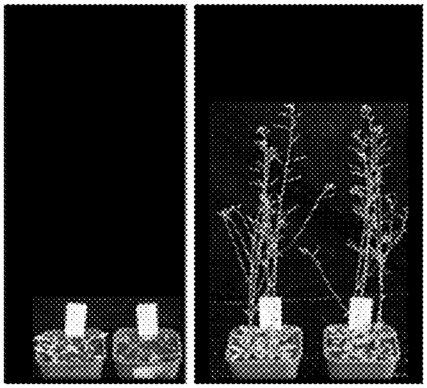

Arabidopsis thaliana(At)-1x Sul.
(Sulfometuron-methyl)
Wild-type SUM1-01

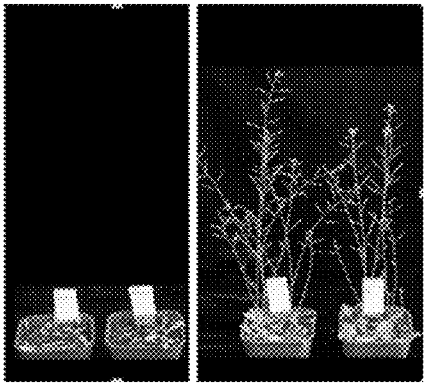

Arabidopsis thaliana(At)-1x Hal.
(Halosulfuron-methyl)
Wild-type SUM1-01

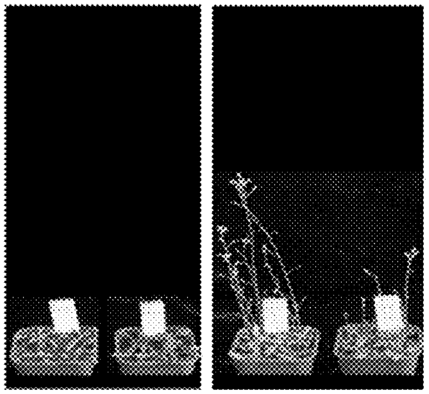

Arabidopsis thaliana(At)-1x Pyr.
(Pyrazosulfuron-ethyl)
Wild-type SUM1-01

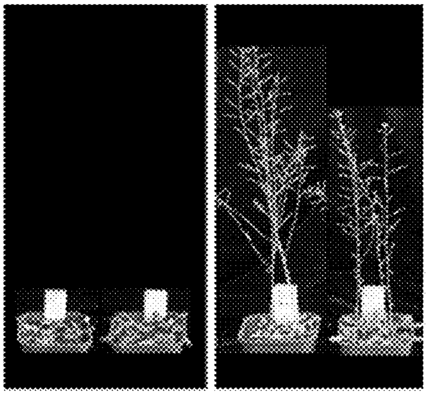

Arabidopsis thaliana(At)-1x Thi.
(Thifensulfuron-methyl)
Wild-type SUM1-01

FIG. 4-1

SULFONYLUREA HERBICIDE RESISTANT TRANSGENIC PLANTS

CROSS-REFERENCE TO RELATED APPLICATIONS

This application is a § 371 national phase of International Application No. PCT/CN2016/109176, filed on Dec. 9, 2016, which claims priority to Chinese invention patent application No. CN105802933A filed Mar. 22, 2016, which applications are incorporated by reference herein in their entireties.

TECHNICAL FIELD

The present invention relates to a herbicide tolerant protein, a coding gene thereof and a use thereof, particularly to a sulfonylurea herbicide tolerant protein, a coding gene thereof and a use thereof.

BACKGROUND ART

Weeds may exhaust valuable nutrients required by crops and other plants of interest in the soil rapidly. Currently, there are many types of herbicides used to control weeds, among which a particularly popular herbicide is glyphosate. Crops resistant to glyphosate have been developed, such as maize, soybean, cotton, sugar beet, wheat, and rice. Therefore, glyphosate can be sprayed onto the field where the glyphosate resistant crops are planted, so as to control weeds without significant damage to the crops.

Glyphosate has been widely used in the world for more than 20 years, resulting in an over-reliance on glyphosate and glyphosate tolerant crop technologies, as well as applying a high selection pressure to plants that are naturally more tolerant to glyphosate or have developed a glyphosate-resistant activity in wild weed species. It has been reported that a few weeds have developed a resistance to glyphosate, including broad-leaved weeds and gramineous weeds, such as *Lolium rigidium, Lolium multiflorum, Eleusine indica* Gaertn, *Ambrosia artemisiifolia, Conyza canadensis, Conyza bonariensis* and *Plantago lanceolata*. Moreover, weeds that were not agricultural problems before the wide use of glyphosate tolerant crops have become prevalent, and are difficult to control with glyphosate tolerant crops, wherein these weeds mainly appear together with (but not only with) difficult-to-control broad-leaved weeds, such as the *Amaranthus, Chenopodium, Dandelion* and *Commelinaceae* species.

In areas where glyphosate resistant weeds or difficult-to-control weed species are present, growers can compensate for the weakness of glyphosate by tank mixing or alternating with other herbicides that can control the missed weeds, such as sulfonylurea herbicides. Sulfonylurea herbicides have become the third most popular herbicides, after organophosphorus and acetamide herbicides, with global annual sales of more than $3 billion. And the annual application area of sulfonylurea herbicides in our country has been more than 2 million hectares and still shows an expanding trend.

With the emergence of glyphosate resistant weeds and the expanding application of sulfonylurea herbicides, there is a need to introduce a sulfonylurea herbicide tolerance into plants of interest that are sensitive to sulfonylurea herbicides. Reports that a herbicide tolerant protein SUM1 is tolerant to sulfonylurea herbicides have not been found yet.

SUMMARY OF THE INVENTION

The objective of the present invention is to provide a herbicide tolerant protein, a coding gene thereof and use thereof, wherein the herbicide tolerant protein SUM1 has a higher tolerance to sulfonylurea herbicides in plants.

In order to achieve the above objective, the present invention provides the following technical solutions.

In one aspect, the present invention provides a herbicide tolerant protein, comprising:

(a) a protein consisting of an amino acid sequence as shown in SEQ ID NO: 1; or (b) a protein which is derived from (a) by substituting and/or deleting and/or adding one or more amino acids in the amino acid sequence of (a), and has the activity of thifensulfuron hydrolase.

In another aspect, the present invention also provides a herbicide tolerant gene, comprising:

(a) a polynucleotide sequence encoding the herbicide tolerant protein; or (b) a polynucleotide sequence as shown in SEQ ID NO: 2; or (c) a polynucleotide sequence as shown in SEQ ID NO: 3.

In another aspect, the present invention provides an expression cassette, comprising the herbicide tolerant gene under regulation of an operably linked regulatory sequence.

In another aspect, the present invention provides a recombinant vector containing the herbicide tolerant gene or the expression cassette.

In another aspect, the present invention also provides a method for producing the herbicide tolerant protein, comprising:

obtaining a cell of a transgenic host organism containing the herbicide tolerant gene or the expression cassette;

cultivating the cell of the transgenic host organism under conditions allowing production of the herbicide tolerant protein;

recovering the herbicide tolerant protein;

preferably, the transgenic host organism comprises plants, animals, bacteria, yeasts, baculoviruses, nematodes, or algae.

In another aspect, the present invention provides a method for increasing the range of herbicides which can be tolerated, comprising: co-expressing the herbicide tolerant protein or the herbicide tolerant protein encoded by the expression cassette with at least one second protein which is different from the herbicide tolerant protein or the herbicide tolerant protein encoded by the expression cassette in a plant;

preferably, the second protein is 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome-like proteins and/or protoporphyrinogen oxidase.

In another aspect, the present invention provides a method for selecting transformed plant cells, comprising: transforming multiple plant cells with the herbicide tolerant gene or the expression cassette, and cultivating the cells under a concentration of the herbicide which allows the growth of the transformed cells expressing the herbicide tolerant gene or the expression cassette, while killing the untransformed cells or inhibiting the growth of the untransformed cells, wherein the herbicide is a sulfonylurea herbicide;

preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention also provides a method for controlling weeds, comprising: applying an effective dose of a sulfonylurea herbicide to a field for planting a target plant, wherein the plant contains the herbicide tolerant gene or the expression cassette;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention also provides a method for protecting a plant from damage caused by a sulfonylurea herbicide, comprising: introducing the herbicide tolerant gene or the expression cassette or the recombinant vector into a plant to make the post-introduction plant produce a sufficient amount of herbicide tolerant protein to prevent the plant from being damaged by the sulfonylurea herbicide;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention provides a method for controlling glyphosate resistant weeds in a field of a glyphosate tolerant plant, comprising: applying an effective dose of a sulfonylurea herbicide to a field for planting the glyphosate tolerant plant, wherein the glyphosate tolerant plant contains the herbicide tolerant gene or the expression cassette;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention also provides a method for imparting sulfonylurea herbicide tolerance to a plant, comprising: introducing the herbicide tolerant gene or the expression cassette or the recombinant vector into the plant;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention provides a method for producing a plant which is tolerant to a sulfonylurea herbicide, comprising introducing the herbicide tolerant gene or the expression cassette or the recombinant vector into the genome of the plant;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention provides a method for cultivating a plant which is tolerant to a sulfonylurea herbicide, comprising: planting at least one plant propagule, the genome of which contains the herbicide tolerant gene or the expression cassette;

allowing the plant propagule to grow into a plant;

applying an effective dose of the sulfonylurea herbicide to a plant growing environment comprising at least the plant, and harvesting the plant having reduced plant damage and/or an increased plant yield compared to other plants without the herbicide tolerant gene or the expression cassette;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention also provides a planting system for controlling weed growth, comprising a sulfonylurea herbicide and a plant growing environment in which at least one target plant exists, wherein the plant contains the herbicide tolerant gene or the expression cassette;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention also provides a planting system for controlling glyphosate resistant weeds in a field of a glyphosate tolerant plant, comprising a sulfonylurea herbicide, a glyphosate herbicide and a field for planting at least one target plant, wherein the glyphosate tolerant plant contains the herbicide tolerant gene or the expression cassette;

preferably, the plant is a monocotyledonous plant or a dicotyledonous plant;

more preferably, the plant is maize, soybean, *Arabidopsis thaliana*, cotton, rape, rice, sorghum, wheat, barley, millet, sugar cane or oats;

further preferably, the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

In another aspect, the present invention provides use of a herbicide tolerant protein for degrading the sulfonylurea herbicides, wherein the herbicide tolerant protein comprises:

(a) a protein consisting of an amino acid sequence as shown in SEQ ID NO: 1; or (b) a protein which is derived from (a) by substituting and/or deleting and/or adding one or more amino acids in the amino acid sequence of (a), and has the activity of thifensulfuron hydrolase.

Preferably, the sulfonylurea herbicides are tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

The herbicide tolerant gene or the expression cassette or the recombinant vector is introduced into a plant. In order to introduce the exogenous DNA into plant cells in the present invention, the conventional transformation methods include, but are not limited to, the *Agrobacterium*-mediated transformation, microprojectile bombardment, the direct DNA uptake into the protoplast, electroporation or silicon whisker-mediated DNA introduction.

The sulfonylurea herbicide tolerant gene and the subsequent herbicide-resistant crop according to the present invention provide an excellent choice for controlling glyphosate-resistant (or highly tolerant and shifted) broad-leaved weed species in the crop. The sulfonylurea herbicides have a broad spectrum and are potent herbicides for broad-leaved weeds, and would provide excellent utility for planters if the stronger crop tolerance could be provided in both dicotyledons and monocotyledons alike. A transgenic dicotyledonous plant with a tolerance to sulfonylurea herbicide also has higher flexibilities in the timing and amount of application. Another use of the sulfonylurea herbicide resistant trait is that it can be used for preventing normally sensitive crops from damage caused by the drifting, volatilization, conversion (or other movement phenomena over a long distance), misuse, destruction, etc., of the sulfonylurea herbicides. The use of a SUM1 gene in a plant can provide protection against a broader spectrum of sulfonylurea herbicides, thereby improving the flexibility and spectra of weeds that can be controlled, and can provide protection against damage caused by the drifting of a full range of commercially available sulfonylurea herbicides or caused by other sulfonylurea herbicides over a long distance.

It has now been identified that the SUM1 gene has the characteristic of allowing the use of sulfonylurea herbicides in plants after being genetically modified for the expression in the plants, wherein the absence or lack of inherent tolerance in the plants does not allow for the use of these herbicides. In addition, the SUM1 gene can provide protection against the sulfonylurea herbicides in plants where the natural tolerance is insufficient for selectivity. At present, the plants containing the SUM1 gene alone can be treated sequentially or tank mixed with one, two or a combination of several sulfonylurea herbicides. The application amount of each sulfonylurea herbicide for controlling a broad spectrum of dicotyledonous weeds ranges from 7.5 to 150 g ai/ha, more generally from 20 to 50 g ai/ha. Use of the herbicides of different chemical categories and having different modes and ranges of actions in the same field in combination (sequentially or tank mixed) can provide control for most potential weeds that need to be controlled by the herbicides.

Glyphosate is widely used, as it controls a very broad spectrum of broad-leaved and gramineous weed species. However, repeat use of glyphosate in glyphosate tolerant crops and in non-crop applications has (and will continue to) selected for weed shifts to naturally more tolerant species or glyphosate resistant biotypes. Most herbicide resistance management strategies suggest using an effective amount of tank-mixed herbicide partners as a means for delaying the emergence of resistant weeds, wherein the herbicide partners provide control for the same species, but have different modes of action. Superposing the SUM1 gene with a glyphosate tolerance trait (and/or other herbicide tolerance traits) can achieve the control of glyphosate resistant weed species (broad-leaved weed species controlled by one or more sulfonylurea herbicides) in glyphosate tolerant crops by enabling the selective use of glyphosate and sulfonylurea herbicides in the same crop. The applications of these herbicides can be performed simultaneously in a tank mixture containing two or more herbicides with different modes of action, or can be performed alone in a single herbicide composition in sequential applications (e.g., before planting, or before or after emergence) (with the interval time of applications ranging from 2 hours to 3 months); or alternatively, the applications of these herbicides can be performed by using a combination of any number of herbicides representative of each applicable compound category at any time (from 7 months after planting a crop to the time when the crop is harvested (or the pre-harvest interval for a single herbicide, wherein the shortest is taken)).

The flexibility in controlling broad-leaved weeds is very important, in terms of the application time, application amount of single herbicide, and abilities for controlling the stubborn or resistant weeds. The application range of glyphosate superposed with a glyphosate resistant gene/SUM1 gene in crops can be from 200 to 1600 g ae/ha. The application range of sulfonylurea herbicides (one or more) can be from 7.5 to 150 g ai/ha. The optimal combination of time for these applications depends on the specific conditions, species and environments.

A herbicide formulation (e.g., an ester, acid or salt-formulation, or soluble concentrate, emulsifying concentrate or soluble liquid) and a tank mix additive (e.g., an adjuvant or compatilizer) can significantly affect the weed control of a given herbicide or a combination of one or more herbicides. Any chemical combination of any of the foregoing herbicides is within the scope of the present invention.

It is well known for a person skilled in the art that the benefits of a combination of two or more modes of action in improving the spectrum of weeds controlled and/or the control of naturally more tolerant species or resistant weed species, can also be extended to chemicals for which herbicide tolerance was enabled in crops through artificial methods (either transgenically or non-transgenically) beyond glyphosate tolerant crops. In fact, the traits encoding the following resistances can be superposed alone or in multiple combinations to provide the ability to effectively control or prevent weed shifts to any of the above categories of herbicides: 5-enolpyruvylshikimate-3-phosphate synthase (EPSPS), glyphosate oxidoreductase (GOX), glyphosate-N-acetyltransferase (GAT), glyphosate decarboxylase, glufosinate acetyltransferase (PAT), α-ketoglutarate-dependent dioxygenase (AAD), dicamba monooxygenase (DMO), 4-hydroxyphenylpyruvate dioxygenase (HPPD), acetolactate synthase (ALS), cytochrome-like proteins (P450) and/or protoporphyrinogen oxidase (Protox).

In addition, the SUM1 gene alone or the SUM1 gene superposed with other characteristics of herbicide resistant crops can be superposed with one or more other input traits (for example, insect resistance, fungal resistance or stress tolerance, etc.) or output traits (for example, increased yield, improved oil amount, increased fiber quality, etc.). Therefore, the present invention can be used to provide complete agricultural solutions for improving the qualities of crops with the abilities for flexibly and economically controlling any number of agriculture pests.

The SUM1 gene of the present invention can degrade sulfonylurea herbicides, which is an important basis for herbicide tolerant crops and selectable marker trait opportunities.

Transgenic expression can be performed in the present invention, and almost all combinations of herbicides for broad-leaved weeds can be controlled. The SUM1 gene as an excellent trait of herbicide tolerant crops can be superposed with, for example, other traits of herbicide tolerant crops (for example, glyphosate resistance, glufosinate resistance, other ALS inhibitor (for example, imidazolinones and triazolopyrimidine sulfonamides) resistances, bromoxynil resistance, HPPD inhibitor resistances, and PPO inhibitor resistances) and traits of insect resistance (Cry1Ab, Cry1F, Vip3, other *Bacillus thuringiensis* proteins or non-*bacillus* genus derived insect resistant proteins, etc.). In addition, the SUM1 gene can be used as a selectable marker for the assistant selection of primary transformants of plants which are genetically modified with another gene or gene group.

The traits of herbicide tolerant crops of the present invention can be used in a new combination with other traits (including, but not limited to, glyphosate tolerance) of herbicide tolerant crops. A new method for controlling the weed species can be produced by the combination of these traits due to a newly obtained resistance or inherent tolerance to a herbicide (for example, glyphosate). Therefore, apart from the traits of herbicide tolerant crops, the scope of the present invention includes the new method for controlling weeds with herbicides, wherein the tolerance to the herbicides can be produced by the enzyme in the transgenic crops.

The present invention can be applied to various types of plants, and the dicotyledonous plant includes, but is not limited to, alfalfa, beans, cauliflowers, cabbages, carrots, celery, cotton, cucumbers, eggplants, lettuces, melon, peas, peppers, zucchinis, radishes, rape, spinach, soybeans, pumpkins, tomatoes, *Arabidopsis thaliana* or watermelons; preferably, the dicotyledonous plant refers to soybeans, *Arabidopsis thaliana*, tobacco, cotton or rape. The monocotyledonous plant includes, but is not limited to, maize, rice, sorghum, wheat, barley, rye, millet, sugar cane, oats or turfgrass. Preferably, the monocotyledonous plant refers to maize, rice, sorghum, wheat, barley, millet, sugar cane or oats. The SUM1 genes of the present invention can be more positively used in gramineous crops with moderate tolerance, and thus the improved tolerance obtained by such traits can provide planters with the possibility of using these herbicides with a more effective application amount and a broader application time without crop damage risks.

The planting system in the present invention refers to a combination of a plant and any herbicide tolerance thereof and/or an available herbicide treatment in different plant developmental stages, thus producing a high-yielding and/or damage-reduced plant.

In the present invention, weeds refer to plants competing with the cultivated target plants in the plant growth environment.

The term "control" and/or "prevention" in the present invention refers to at least a direct application of (e.g., by spraying) an effective dose of a sulfonylurea herbicide to the plant growth environment, so as to minimize weed development and/or stop weeds from growing. At the same time, the cultivated target plants should be morphologically normal and can be cultivated under conventional methods for product consumption and/or production; and preferably, compared to non-transgenic wild-type plants, the cultivated plants have reduced plant damage and/or an increased plant yield. The specific performances of the reduced plant damage include, but are not limited to, an improved stem resistance and/or an increased grain weight, etc. The "control" and/or "prevention" effect of the herbicide tolerant protein SUM1 on weeds can exist independently, and will not be diminished and/or lost due to the presence of other substances that can "control" and/or "prevent" the weeds. Specifically, if any tissue of a transgenic plant (containing the SUM1 gene) has and/or produces the herbicide tolerant protein SUM1 and/or another substance that can control weeds simultaneously and/or separately, then the presence of the other substance will neither affect the "control" and/or "prevention" effect of the herbicide tolerant protein SUM1 on the weeds, nor result in the "control" and/or "prevention" effect being completely and/or partially achieved by the other substance, regardless of the herbicide tolerant protein SUM1.

The genome of a plant, plant tissue or plant cell in the present invention refers to any genetic material within the plant, plant tissue or plant cell, and includes nuclear, plastid and mitochondrial genomes.

The "plant propagule" in the present invention includes, but is not limited to, plant sexual propagules and plant vegetative propagules. The plant sexual propagules include, but are not limited to, plant seeds; and the plant vegetative propagules refer to vegetative organs or a specific tissue of a plant, which can generate a new plant under ex vivo conditions. The vegetative organs or the specific tissue include, but are not limited to, roots, stems and leaves, for example: plants with roots as the vegetative propagules including strawberries, sweet potatoes and the like; plants with stems as the vegetative propagules including sugar cane, potatoes (tubers) and the like; and plants with leaves as the vegetative propagules including aloe, begonias and the like.

The "resistance" in the present invention is heritable, and allows a plant to grow and propagate in the case where an effective treatment by a general herbicide is performed on a given plant. As recognized by a person skilled in the art, even if a certain degree of damage of a plant treated with a herbicide is apparent, the plant can still be considered to be "resistant". The term "tolerant" or "tolerance" in the present invention is more extensive than the term "resistance", and includes "resistance" and an improved ability of a particular plant to resist various degrees of damage induced by a herbicide, and in general, damage to a wild-type plant with the same genotype can be caused at the same herbicide dose.

The polynucleotide and/or nucleotide in the present invention form a complete "gene", which encodes a protein or a polypeptide in a desired host cell. A person skilled in the art will readily appreciate that the polynucleotide and/or nucleotide in the present invention can be placed under the control of a regulatory sequence in a host of interest.

As is well known to a person skilled in the art, DNA is typically present in a double-stranded form. In this arrangement, one strand is complementary to the other, and vice versa. Additional complementary strand of DNA is produced as DNA is replicated in a plant. As such, the present invention includes the use of the polynucleotides as exemplified in the sequence listing and complementary strands thereof. The "coding strand" commonly used in the art refers to a strand bound to an anti-sense strand. In order to express a protein in vivo, one strand of DNA is typically transcribed to one complementary strand of mRNA, which acts as a template for translating the protein. Actually, mRNA is transcribed from the "anti-sense" strand of DNA. The "sense" or "coding" strand has a series of codons (a codon is composed of three nucleotides, and a specific amino acid can be produced by reading three codons at a time), which can be read as an open reading frame (ORF) to form a protein or peptide of interest. The present invention also includes RNA with an equivalent function to the exemplary DNA.

The nucleic acid molecule or a fragment thereof in the present invention hybridizes with the herbicide tolerant gene of the present invention under stringent conditions. Any conventional nucleic acid hybridization or amplification method can be used to identify the presence of the herbicide tolerant gene of the present invention. A nucleic acid molecule or a fragment thereof is capable of specifically hybridizing with other nucleic acid molecules under certain circumstances. In the present invention, if two nucleic acid molecules can form an anti-parallel double-stranded nucleic acid structure, then it can be considered that these two nucleic acid molecules can be specifically hybridized with each other. If two nucleic acid molecules exhibit a complete complementarity, then one nucleic acid molecule of the two is said to be the "complement" of the other nucleic acid molecule. In the present invention, when each nucleotide of a nucleic acid molecule is complementary to the corresponding nucleotide of another nucleic acid molecule, then these two nucleic acid molecules are said to exhibit a "complete complementarity". If two nucleic acid molecules can be hybridized with each other with a sufficient stability to allow them to anneal and bind with each other at least under conventional "low stringency" conditions, then these two nucleic acid molecules are said to be "minimally complementary". Similarly, if two nucleic acid molecules can be hybridized with each other with a sufficient stability to allow them to anneal and bind with each other under conventional "high stringency" conditions, then these two nucleic acid molecules are said to be "complementary". Deviation from a complete complementarity is permissible, as long as this deviation does not completely prevent two molecules from forming a double-stranded structure. In order to enable a nucleic acid molecule to act as a primer or probe, it is only guaranteed that the molecule has a sufficient complementarity in its sequence to allow a stable double-stranded structure to be formed under the conditions of particular solvent and salt concentration.

In the present invention, a substantially homologous sequence is a nucleic acid molecule, wherein the nucleic acid molecule can be specifically hybridized with the complementary strand of a matched nucleic acid molecule under high stringency conditions. Suitable stringent conditions that promote DNA hybridization are well known to a person skilled in the art; for example, the suitable stringent conditions can be achieved by treating with 6.0× sodium chloride/sodium citrate (SSC) under conditions of approximately 45° C., and then washing with 2.0×SSC under conditions of 50° C. For example, the salt concentration in the washing step can be selected from the low stringency condition of about 2.0×SSC and 50° C. to the high stringency condition of about 0.2×SSC and 50° C. In addition, the temperature condition in the washing step can rise from the low stringency condition of room temperature (about 22° C.) to the high stringency condition of about 65° C. The temperature condition and the salt concentration can both vary, and it is also possible that one of the two remains unchanged, while the other variable varies. Preferably, the stringent conditions in the present invention can be achieved by specifically hybridizing a sequence with the SUM1 gene in the present invention in a 6×SSC, 0.5% SDS solution at 65° C., and then washing the membrane each once with 2×SSC, 0.1% SDS and 1×SSC, 0.1% SDS.

Consequently, sequences which have the herbicide tolerant activity and are hybridized with the SUM1 gene of the present invention under stringent conditions are included in the present invention. These sequences are at least approximately 40%-50% homologous, or approximately 60%, 65% or 70% homologous to the sequence of the present invention, and even have a sequence homology of at least approximately 75%, 80%, 85%, 90%, 91%, 92%, 93%, 94%, 95%, 96%, 97%, 98%, 99% or more with the sequence of the present invention.

The present invention provides a functional protein. In the present invention, the "functional activity" (or "activity") means that the protein/enzyme used in the present invention (alone or in combination with other proteins) has the ability to degrade a herbicide or diminish the herbicide activity. A plant producing the protein of the present invention preferably produces an "effective amount" of the protein, so that when treating the plant with a herbicide, the protein expression level is sufficient to confer the plant with a complete or partial resistance or tolerance to the herbicide (unless otherwise specified, in a general amount). The herbicide can be used in an amount which would usually kill a target plant or in a normal field amount and concentration. Preferably, the plant cell and plant of the present invention are protected from growth inhibition or damage caused by treatment with the herbicide. The transformed plant and plant cell of the present invention are preferably tolerant or resistant to sulfonylurea herbicides, that is, the transformed plant and plant cell can grow in the presence of an effective amount of sulfonylurea herbicides.

The gene and protein in the present invention not only comprise a specific exemplary sequence, but also comprise a portion and/or a fragment (including an internal deletion and/or terminal deletion compared to the full-length protein), a variant, a mutant, a substitute (a protein having substituted amino acids), a chimera and a fusion protein, which retain the herbicide tolerance activity characteristic of the specific exemplary protein. The "variant" or "variation" refers to a nucleotide sequence that encodes the same protein or encodes an equivalent protein having a herbicide resistance activity. The "equivalent protein" refers to a protein having the same or substantially the same bioactivity of herbicide tolerance as the claimed protein.

The "fragment" or "truncation" of a DNA molecule or protein sequence in the present invention refers to a portion of the original DNA or protein sequence (nucleotides or amino acids) or an artificially modified form thereof (e.g., a sequence suitable for plant expression), wherein the length of the foregoing sequences may vary, but the length is sufficient to ensure that the (encoded) protein is a herbicide tolerant protein.

Because of the degeneracy of the genetic codon, a variety of different DNA sequences may encode the same amino acid sequence. It is within the skill of a person skilled in the art to produce these alternative DNA sequences encoding the same or substantially the same protein. These different DNA sequences are included in the scope of the present invention. The "substantially the same" sequence refers to a sequence with an amino acid substitution, deletion, addition or insertion that does not substantively affect the herbicide tolerance activity, and includes a fragment retaining the herbicide tolerance activity.

The substitution, deletion or addition of an amino acid sequence in the present invention is a conventional technique in the art, and preferably, this amino acid change is: a small characteristic change, that is, a conservative amino acid substitution that does not significantly affect the folding and/or activity of a protein; a small deletion, typically a deletion of about 1-30 amino acids; a small amino or carboxyl terminal extension, e.g., a methionine residue extending at the amino terminus; or a small linker peptide, e.g., about 20-25 residues in length.

Examples of conservative substitutions are substitutions occurring within the following amino acid groups: basic amino acids (e.g., arginine, lysine and histidine), acidic amino acids (e.g., glutamic acid and aspartic acid), polar amino acids (e.g., glutamine and asparagine), hydrophobic amino acids (e.g., leucine, isoleucine and valine), aromatic amino acids (e.g., phenylalanine, tryptophan and tyrosine) and small molecule amino acids (e.g., glycine, alanine, serine, threonine and methionine). Those amino acid substitutions that generally do not alter the specific activity are well known in the art, and have been described, for example, by N. Neurath and R. L. Hill in "Protein", published by Academic Press, New York, 1979. The most common substitutions are Ala/Ser, Val/Ile, Asp/Glu, Thu/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, as well as the reverse substitutions thereof.

As will be apparent to a person skilled in the art, this substitution can occur outside the region that is important for molecular functions, and still produces an active polypeptide. Amino acid residues that are essential for the activity of the polypeptide of the present invention and are thus chosen not to be substituted can be identified according to methods known in the art, such as site-directed mutagenesis or alanine-scanning mutagenesis (see e.g., Cunningham and Wells, 1989, Science 244: 1081-1085). The latter technique is to introduce a mutation to each positively charged residue in a molecule and detect the herbicide resistance activity of the resulting mutant molecule to determine the amino acid residues that are important for the molecular activity. Substrate-enzyme interaction sites can also be determined by analyzing the three-dimensional structure thereof, wherein this three-dimensional structure can be determined by nuclear magnetic resonance analysis, crystallography, photoaffinity labeling and other techniques (see e.g., de Vos et al., 1992, Science 255: 306-312; Smith et al., 1992, J. Mol. Biol. 224: 899-904; and Wlodaver et al., 1992, FEBS Letters 309: 59-64).

The regulatory sequence in the present invention includes, but is not limited to, a promoter, a transit peptide, a terminator, an enhancer, a leader sequence, an intron and other regulatory sequences operably linked to the SUM1 gene.

The promoter is a plant expressible promoter. The "plant expressible promoter" refers to a promoter that ensures the expression of the coding sequence linked thereto in a plant cell. The plant expressible promoter can be a constitutive promoter. Examples of the promoters directing the constitutive expression in plants include, but are not limited to, a 35S promoter derived from a cauliflower mosaic virus, maize Ubi promoters, rice GOS2 gene promoters, and the like. Alternatively, the plant expressible promoter can be a tissue specific promoter, i.e. the promoter directs the expression of an coding sequence in several tissues, such as green tissues, at a level higher than in other tissues of the plant (which can be measured through conventional RNA trials), such as a PEP carboxylase promoter. Alternatively, the plant expressible promoter can be a wound-inducible promoter. The wound-inducible promoter or a promoter directing a wound-induced expression pattern means that when a plant suffers from a wound caused by a mechanical factor or the gnawing of insects, the expression of the coding sequence under the regulation of the promoter is significantly improved compared to normal growth conditions. Examples of the wound-inducible promoters include, but are not limited to, promoters of potato and tomato protease inhibitor genes (pin I and pin II) and a maize protease inhibitor gene (MPI).

The transit peptide (also known as secretion signal sequence or targeting sequence) directs a transgenic product to a specific organelle or cell compartment. For a receptor protein, the transit peptide may be heterologous, for example, targeting the chloroplast using a sequence encoding the chloroplast transit peptide, or targeting the endoplasmic reticulum using a 'KDEL' retention sequence, or targeting the vacuole using CTPP of a barley phytolectin gene.

The leader sequence includes, but is not limited to, a small RNA virus leader sequence, such as an EMCV leader sequence (a 5' non-coding region of encephlomyocarditis virus); a potato virus Y group leader sequence, such as a MDMV (Maize Dwarf Mosaic Virus) leader sequence; human immunoglobulin heavy chain binding protein (BiP); an untranslated leader sequence of the coat protein mRNA of alfalfa mosaic virus (AMV RNA4); and a tobacco mosaic virus (TMV) leader sequence.

The enhancer includes, but is not limited to, a cauliflower mosaic virus (CaMV) enhancer, figwort mosaic virus (FMV) enhancer, carnation etched ring virus (CERV) enhancer, cassava vein mosaic virus (CsVMV) enhancer, *mirabilis* mosaic virus (MMV) enhancer, cestrum yellow leaf curling virus (CmYLCV) enhancer, cotton leaf curl Multan virus (CLCuMV) enhancer, *commelina* yellow mottle virus (CoYMV) enhancer and peanut chlorotic streak caulimovirus (PCLSV) enhancer.

For use in a monocotyledonous plant, the intron includes, but is not limited to, a maize hsp70 intron, maize ubiquitin intron, Adh intron 1, sucrose synthase intron or rice Act1 intron. For use in a dicotyledonous plant, the intron includes, but is not limited to, a CAT-1 intron, pKANNIBAL intron, PIV2 intron and "super ubiquitin" intron.

The terminator can be a suitable polyadenylation signal sequence that functions in a plant, including, but not limited to, a polyadenylation signal sequence derived from the *Agrobacterium tumefaciens* nopaline synthetase (NOS) gene, a polyadenylation signal sequence derived from the protease inhibitor II (pinII) gene, a polyadenylation signal sequence derived from the pea ssRUBISCO E9 gene and a polyadenylation signal sequence derived from the $\alpha$-tubulin gene.

The "effectively linking" in the present invention indicates the binding of nucleic acid sequences, wherein the binding enables a sequence to provide a function required for the sequence linked thereto. The "effectively linking" in the present invention can be achieved by linking a promoter to a sequence of interest, so that the transcription of the sequence of interest is controlled and regulated by the promoter. When a sequence of interest encodes a protein and the expression of the protein is desired, "effectively linking" means that: a promoter is linked to the sequence in such a manner that the resulting transcript is efficiently translated. If the linking of a promoter to a coding sequence is a transcript fusion and expression of the encoded protein is intended to be achieved, such linking is created that the first translation initiation codon in the resulting transcript is the initiation codon in the coding sequence. Alternatively, if the linking of a promoter to a coding sequence is a translation fusion and expression of the encoded protein is intended to be achieved, such a linking is created that the first translation initiation codon contained in the 5' untranslated sequence is linked to the promoter in such a manner that the relationship of the resulting translation product with the translation open reading frame encoding the desired protein is an in-frame. Nucleic acid sequences that can be "effectively linked" include, but are not limited to: sequences providing gene expression functions (i.e., gene expression elements, such as promoters, 5' untranslated regions, introns, protein coding regions, 3' untranslated regions, polyadenylation sites and/or transcription terminators), sequences providing DNA transfer and/or integration functions (i.e., T-DNA boundary sequences, site-specific recombinase recognition sites and integrase recognition sites), sequences providing selective functions (i.e., antibiotic resistance markers and biosynthesis genes), sequences providing marker scoring functions, sequences assisting in sequence manipulation in vitro or in vivo (i.e., polylinker sequences and site-specific recombination sequences), and sequences providing replication functions (i.e., the bacterial origins of replication, autonomously replicating sequences and centromeric sequences).

The present invention may confer a new herbicide resistance trait to a plant, and no adverse effects on the phenotypes (including yields) are observed. The plant in the present invention can tolerate, e.g., 2×, 3×, 4× or 5× the general application level of at least one herbicide tested. The improvement of these levels of tolerance is within the scope of the present invention. For example, foreseeable optimization and further development can be performed on various techniques known in the art, in order to increase the expression of a given gene.

In the present invention, the herbicide tolerant protein is of the SUM1 amino acid sequence as shown in SEQ ID NO: 1 in the sequence listing. The herbicide tolerant gene is of the SUM1 nucleotide sequence as shown in SEQ ID NO: 2 and SEQ ID NO: 3 in the sequence listing. The herbicide tolerant gene can be used for plants; and apart from a coding region of proteins encoded by the SUM1 nucleotide sequence, the gene can also contain other elements, for example, a coding region encoding a transit peptide, a coding region encoding a selective marker protein or a protein imparting insect resistance.

The herbicide tolerant protein SUM1 in the present invention is tolerant to most of the sulfonylurea herbicides. The plant in the present invention contains an exogenous DNA in its genome, wherein the exogenous DNA comprises the SUM1 nucleotide sequence, and the plant is protected from the threat of a herbicide by expressing an effective amount of the protein. The effective amount refers to a dose causing no or minor damage. At the same time, the plant should be morphologically normal and can be cultivated under conventional methods for product consumption and/or production.

The expression level of the herbicide tolerant protein in a plant material can be detected by a variety of methods described in the art, for example, by quantifying the mRNA encoding the herbicide tolerant protein produced in a tissue by applying specific primers, or specifically detecting the amount of the herbicide tolerant protein produced directly.

The present invention provides a herbicide tolerant protein, a coding gene thereof and a use thereof, having the following advantages:

1. Having a strong herbicide tolerance. The herbicide tolerant protein SUM1 of the present invention has a strong tolerance for sulfonylurea herbicides and can tolerate four-fold field concentration.

2. Having a broad herbicide tolerance. The herbicide tolerant protein SUM1 of the present invention can exhibit a higher resistance to a plurality of sulfonylurea herbicides, and thus has a broad application prospect in plants.

The technical solution of the present invention is further described in details through the drawings and examples below.

DESCRIPTION OF THE DRAWINGS

FIG. 4-1 and FIG. 4-2 are diagrams showing the tolerance of a transgenic *Arabidopsis thaliana* $T_1$ plant to sulfonylurea herbicides for the herbicide tolerant protein, the coding gene thereof and a use thereof in the present invention;

PARTICULAR EMBODIMENTS

The present invention is further illustrated through the following specific examples. However, it should be understood that the examples are used for illustrating the present invention in more detail, but not intended to limit the protection scope of the invention in any way.

The materials and experimental methods used in the experiments of the invention are described generally in this section. Although many materials and methods used for the invention are well known in the art, they will still be described herein in as much detail as possible. It would be clear to one skilled in the art that unless indicated otherwise in the context, the materials and methods used in the invention are well known in the art.

The technical solutions of the herbicide tolerant protein, the coding gene thereof and a use thereof in the present invention are further described through specific examples below.

Example 1. Acquisition and Synthesis of a SUM1 Gene Sequence

1. Acquisition of the SUM1 Gene Sequence

The amino acid sequence (350 amino acids) of the herbicide tolerant protein SUM1 is shown as SEQ ID NO: 1 in the sequence listings; the SUM1-01 nucleotide sequence (1053 nucleotides) as shown in SEQ ID NO: 2 in the sequence listings encoding the amino acid sequence corresponding to the herbicide tolerant protein SUM1 was obtained based on the soybean codon usage bias, and the SUM1-02 nucleotide sequence (1053 nucleotides) as shown in SEQ ID NO: 3 in the sequence listings encoding the amino acid sequence corresponding to the herbicide tolerant protein SUM1 was obtained based on the maize codon usage bias.

2. Synthesis of the Above-Mentioned Nucleotide Sequences

The SUM1-01 nucleotide sequence (as shown in SEQ ID NO: 2 in the sequence listings) and the SUM1-02 nucleotide sequence (as shown in SEQ ID NO: 3 in the sequence listings) were synthesized by Nanjing Genscript Biotechnology Co., Ltd.; the synthetic SUM1-01 nucleotide sequence (SEQ ID NO: 2) is further connected with a SpeI restriction site at the 5' end, and the SUM1-01 nucleotide sequence (SEQ ID NO: 2) is further connected with a KasI restriction site at the 3' end; and the synthetic SUM1-02 nucleotide sequence (SEQ ID NO: 3) is further connected with a SpeI restriction site at the 5' end, and the SUM1-02 nucleotide sequence (SEQ ID NO: 3) is further connected with a KasI restriction site at the 3' end.

Example 2. Construction of Recombinant Expression Vectors for *Arabidopsis thaliana*

Figure 1:
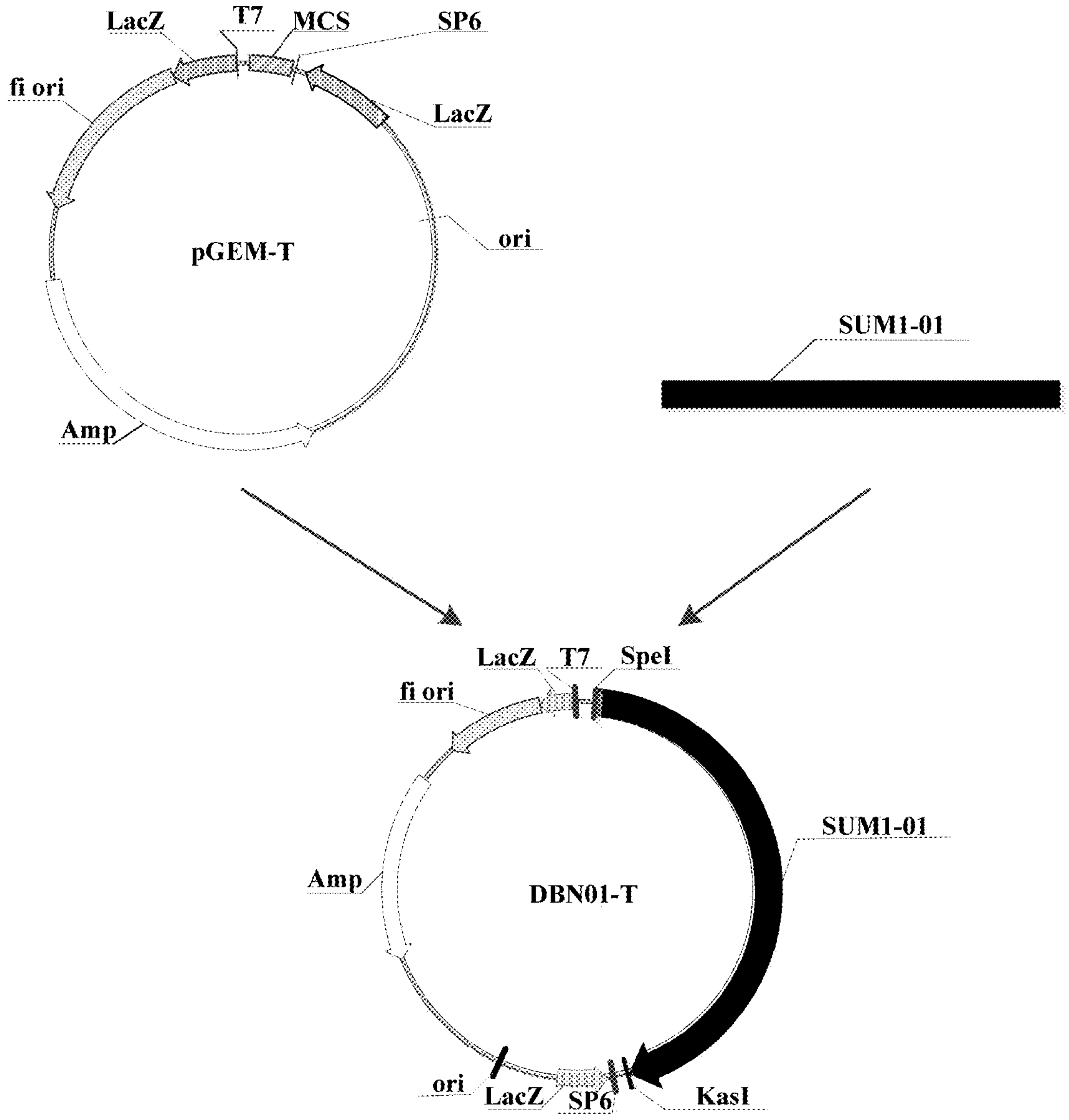
FIG. 1 is a construction flow chart of a recombinant cloning vector DBN01-T containing a SUM1 nucleotide sequence for the herbicide tolerant protein, the coding gene thereof and a use thereof in the present invention.

1. Construction of Recombinant Cloning Vectors Containing SUM1 Nucleotide Sequences for *Arabidopsis thaliana* and Soybean The synthetic SUM1-1-01 nucleotide sequence was ligated into cloning vector pGEM-T (Promega, Madison, USA, CAT: A3600), and the operational procedure was carried out according to Promega's pGEM-T vector product instructions, thus obtaining a recombinant cloning vector DBN01-T, the construction process of which was as shown in FIG. 1 (wherein, Amp represents the ampicillin resistance gene; f1 represents the origin of replication of phage f1; LacZ is LacZ initiation codon; SP6 is SP6 RNA polymerase promoter; T7 is T7 RNA polymerase promoter; the SUM1-01 is the SUM1-01 nucleotide sequence (SEQ ID NO: 2); and MCS is a multiple cloning site).

Then, *Escherichia coli* T1 competent cells (Transgen, Beijing, China, CAT: CD501) were transformed with the recombinant cloning vector DBN01-T using the heat shock method under the following heat shock conditions: water bathing 50 μL of *Escherichia coli* T1 competent cells and 10 μL of plasmid DNA (recombinant cloning vector DBN01-T) at 42° C. for 30 seconds; shake culturing at 37° C. for 1 hour (using a shaker at a rotation speed of 100 rpm for shaking); and growing on an LB plate (10 g/L of tryptone, 5 g/L of yeast extract, 10 g/L of NaCl, and 15 g/L of agar, and adjusting the pH to 7.5 with NaOH) of ampicillin (100 mg/L) having its surface coated with IPTG (isopropylthio-β-D-galactoside) and X-gal (5-bromo-4-chloro-3-indole-β-D-galactoside) overnight. White colonies were picked out and cultured in an LB liquid culture medium (10 g/L of tryptone, 5 g/L of yeast extract, 10 g/L of NaCl, and 100 mg/L of ampicillin, and adjusting the pH to 7.5 with NaOH) at a temperature of 37° C. overnight. The plasmids in the cells were extracted through an alkaline method: centrifuging the bacteria solution at a rotation speed of 12000 rpm for 1 min, removing the supernatant, and suspending the precipitated thalli with 100 μL of ice pre-cooled solution I (25 mM Tris-HCl, 10 mM EDTA (ethylenediaminetetraacetic acid), and 50 mM glucose, with a pH of 8.0); adding 200 μL of newly formulated solution II (0.2M NaOH, 1% SDS (sodium dodecyl sulfate)), inverting the tube 4 times, and mixing and placing on ice for 3-5 min; adding 150 μL of ice-cold solution III (3 M potassium acetate, 5 M acetic acid), mixing uniformly immediately and placing on ice for 5-10 min; centrifuging under the conditions of a temperature of 4° C. and a rotation speed of 12000 rpm for 5 min, adding 2 volumes of anhydrous ethanol to the supernatant and placing at room temperature for 5 min after mixing uniformly; centrifuging under the conditions of a temperature of 4° C. and a rotation speed of 12000 rpm for 5 min, discarding the supernatant, and air drying the precipitate after washing with ethanol with a concentration of 70% (V/V); adding 30 μL of TE (10 mM Tris-HCl, and 1 mM EDTA, with a pH of 8.0) containing RNase (20 μg/mL) to dissolve the precipitate; water bathing at a temperature of 37° C. for 30 min to digest the RNA; and storing at a temperature of −20° C. for use.

After identifying the extracted plasmid by SpeI and KasI digestion, positive clones were verified by sequencing. The results showed that the inserted SUM1-01 nucleotide sequence in the recombinant cloning vector DBN01-T was the nucleotide sequence as shown in SEQ ID NO: 2 in the sequence listings, that is, the SUM1-01 nucleotide sequence was inserted correctly.

2. Construction of Recombinant Expression Vectors Containing SUM1 Nucleotide Sequences for *Arabidopsis thaliana*

Figure 2:
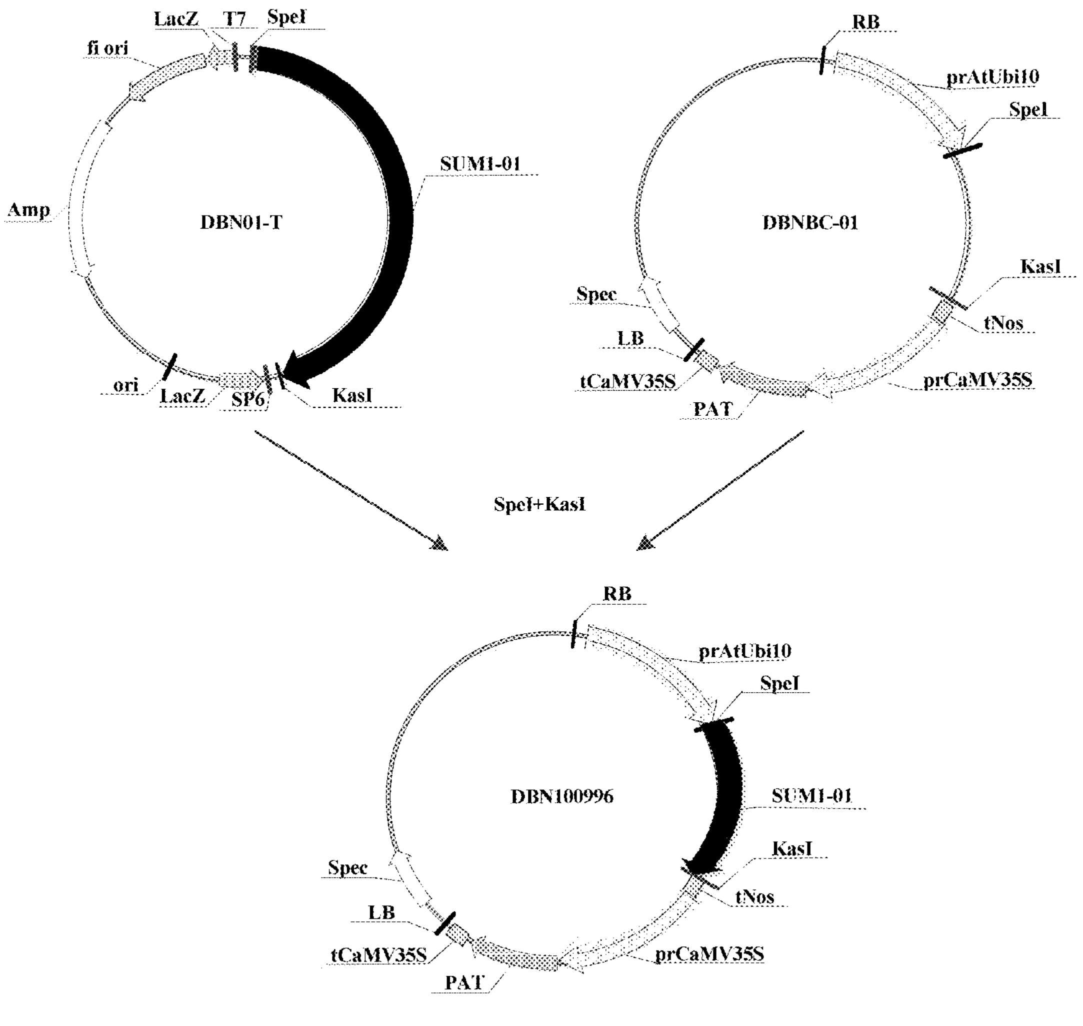
FIG. 2 is a construction flow chart of a recombinant expression vector DBN100996 containing a SUM1 nucleotide sequence for the herbicide tolerant protein, the coding gene thereof and a use thereof in the present invention.

The recombinant cloning vector DBN01-T and an expression vector DBNBC-01 (vector backbone: pCAMBIA2301 (which can be provided by the CAMBIA institution)) were both digested with restriction enzymes SpeI and KasI; the excised SUM1-01 nucleotide sequence fragment was inserted between the SpeI and KasI sites in the expression vector DBNBC-01; and it is well known to a person skilled in the art to construct a vector using conventional enzyme digestion methods, wherein a recombinant expression vector DBN100996 was constructed, and the construction process of which was as shown in FIG. 2 (Spec: the spectinomycin gene; RB: the right boundary; prAtUbi10: the *Arabidopsis thaliana* Ubiquitin 10 gene promoter (SEQ ID NO: 4); SUM1-01: the SUM1-01 nucleotide sequence (SEQ ID NO: 2); tNos: the terminator of a nopaline synthase gene (SEQ ID NO:5); prCaMV35S: the cauliflower mosaic virus 35S promoter (SEQ ID NO: 6); PAT: the glufosinate acetyltransferase gene (SEQ ID NO: 7); tCaMV35S: the cauliflower mosaic virus 35S terminator (SEQ ID NO: 8); LB: the left boundary).

*Escherichia coli* T1 competent cells were transformed with the recombinant expression vector DBN100996 by a heat shock method under the following heat shock conditions: water bathing 50 μL of *Escherichia coli* T1 competent cells and 10 μL of plasmid DNA (recombinant expression vector DBN100996) at 42° C. for 30 seconds; shake culturing at 37° C. for 1 hour (using a shaker at a rotation speed of 100 rpm for shaking); then culturing under the condition of a temperature of 37° C. on an LB solid plate containing 50 mg/L of spectinomycin (10 g/L of tryptone, 5 g/L of yeast extract, 10 g/L of NaCl, and 15 g/L of agar, and adjusted to a pH of 7.5 with NaOH) for 12 hours, picking white colonies, and culturing under the condition of a temperature of 37° C. overnight in an LB liquid culture medium (10 g/L of tryptone, 5 g/L of yeast extract, 10 g/L of NaCl, and 50 mg/L of spectinomycin, and adjusted to a pH of 7.5 with NaOH). The plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant expression vector DBN100996 was the nucleotide sequence as shown in SEQ ID NO: 2 in the sequence listings, i.e., the SUM1-01 nucleotide sequence.

3. Construction of Recombinant Expression Vectors Containing Control Sequences for *Arabidopsis thaliana*

The recombinant cloning vector DBN01R1-T containing control sequence 1 and the recombinant cloning vector DBN01R2-T containing control sequence 2 were constructed using control sequence 1 (SEQ ID NO: 9) and control sequence 2 (SEQ ID NO: 10) respectively, according to the method for constructing the recombinant cloning vector DBN01-T containing the SUM1 nucleotide sequence as described in Example 1. Positive clones were validated by sequencing, with the results showing that the control sequence 1 inserted into the recombinant cloning vector DBN01R1-T was the nucleotide sequence as shown in SEQ ID NO: 9 in the sequence listings, and the control sequence 2 inserted into the recombinant cloning vector DBN01R2-T was the nucleotide sequence as shown in SEQ ID NO: 10 in the sequence listings, i.e., the control sequences were inserted correctly.

Figure 3:
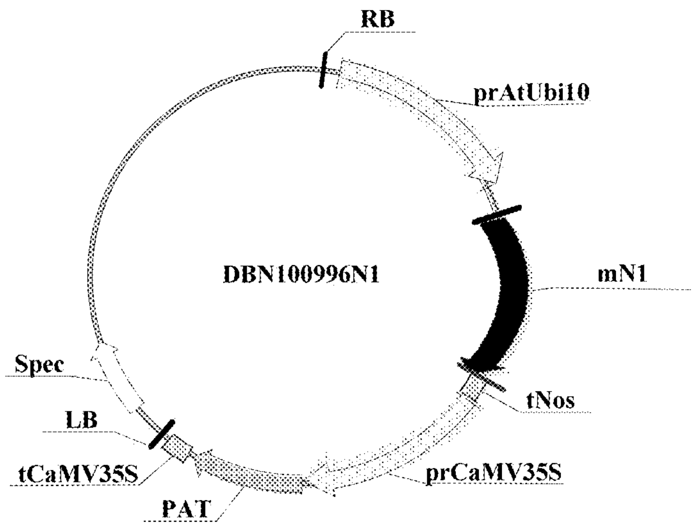
FIG. 3 is a schematic structural diagram of a recombinant expression vector DBN100996N1 containing a control sequence 1 for the herbicide tolerant protein, the coding gene thereof and a use thereof in the present invention.

The recombinant expression vector DBN100996N1 containing control sequence 1 was constructed using control sequence 1 according to the method for constructing the recombinant expression vector DBN100996 containing the SUM1 nucleotide sequence as described in Example 2, and has a structure as shown in FIG. 3 (vector backbone: pCAMBIA2301 (which can be provided by the CAMBIA institution); Spec: the spectinomycin gene; RB: the right boundary; prAtUbi10: the *Arabidopsis thaliana* Ubiquitin 10 gene promoter (SEQ ID NO: 4); mN1: control sequence 1 (SEQ ID NO: 9); tNos: the terminator of a nopaline synthase gene (SEQ ID NO:5); prCaMV35S: the cauliflower mosaic virus 35S promoter (SEQ ID NO: 6); PAT: the glufosinate acetyltransferase gene (SEQ ID NO: 7); tCaMV35S: the cauliflower mosaic virus 35S terminator (SEQ ID NO: 8); LB: the left boundary). Positive clones were validated by sequencing, with the results showing that the control sequence 1 inserted into the recombinant expression vector DBN100996N1 was the nucleotide sequence as shown in SEQ ID NO: 9 in the sequence listings, i.e., the control sequence 1 was inserted correctly.

The recombinant expression vector DBN100996N2 containing control sequence 2 was constructed using the control sequence 2 according to the method for constructing the recombinant expression vector DBN100996N1 containing control sequence 1 as described above. Positive clones were validated by sequencing, with the results showing that the control sequence 2 inserted into the recombinant expression vector DBN100996N2 was the nucleotide sequence as shown in SEQ ID NO: 10 in the sequence listings, i.e., the control sequence 2 was inserted correctly.

Example 3. Acquisition of *Arabidopsis thaliana* Plants Having an SUM1 Nucleotide Sequence Introduced 1. Transformation of *Agrobacterium* with the Recombinant Expression Vectors The *Agrobacterium* GV3101 was transformed with the recombinant expression vectors DBN100996, DBN100996N1 and DBN100996N2, which had been correctly constructed using the liquid nitrogen method, with the following transformation conditions: placing 100 μL of *Agrobacterium* GV3101, and 3 μL of plasmid DNA (recombinant expression vector) in liquid nitrogen for 10 minutes, and warm water bathing at 37° C. for 10 minutes; inoculating the transformed *Agrobacterium* GV3101 into an LB tube, culturing under the conditions of a temperature of 28° C. and a rotation speed of 200 rpm for 2 hours, spreading on an LB plate containing 50 mg/L of rifampicin and 50 mg/L of spectinomycin until positive single clones were grown, picking out single clones for culturing and extracting the plasmids thereof, and performing enzyme digestion verification using restriction enzymes. The results showed that the structures of the recombinant expression vectors DBN100996, DBN100996N1 and DBN100996N2 were completely correct.

2. Acquisition of Transgenic *Arabidopsis thaliana* Plants

Seeds of wild-type *Arabidopsis thaliana* were suspended in a 0.1% (w/v) agarose solution. The suspended seeds were stored at 4° C. for 2 days to complete the need for dormancy, in order to ensure synchronous seed germination. Vermiculite was mixed with horse manure soil, the mixture was sub-irrigated with water to wet same, and the soil mixture was allowed to drain the water away for 24 hours. The pretreated seeds were sowed in the soil mixture and covered with a moisturizing cover for 7 days. The seeds were germinated and the plants were cultivated in a greenhouse under long day conditions (16 hour light/8 hour dark) at a constant temperature (22° C.) and a constant humidity (40-50%), with a light intensity of 120-150 μmol/($m^2$·sec). The plants were initially irrigated with Hoagland's nutrient solution, followed by deionized water, thus keeping the soil moist, but not wet through.

*Arabidopsis thaliana* was transformed using the flower soaking method. One or more 15-30 mL pre-cultures of a YEP culture solution (containing spectinomycin (50 mg/L) and rifampicin (10 mg/L)) were inoculated with the picked *Agrobacterium* colonies. The cultures were incubated at 28° C. and 220 rpm with shaking at a constant speed overnight. Each pre-culture was used to inoculate two 500 mL cultures of the YEP culture solution (containing spectinomycin (50 mg/L) and rifampicin (10 mg/L)), and the cultures were incubated at 28° C. with continuous shaking overnight. Cells were precipitated by centrifuging at about 8700×g at room temperature for 10 minutes, and the resulting supernatant was discarded. The cell precipitate was gently re-suspended in 500 mL of an osmotic medium which contained ½×MS salt/B5 vitamin, 10% (w/v) sucrose, 0.044 μM of benzylaminopurine (10 μL/L (1 mg/mL, a stock solution in DMSO)) and 300 μL/L of Silvet L-77. About 1-month-old plants were soaked in a culture medium for 15 seconds to ensure immersion of the latest inflorescence. Then, the plants were reclined laterally and covered (transparently or opaquely) for 24 hours, then washed with water, and placed vertically. The plants were cultivated with a photoperiod of 16 hours of light/8 hours of darkness at 22° C. Seeds were harvested after soaking for about 4 weeks.

The newly harvested (SUM1 nucleotide sequence and the control sequence) $T_1$ seeds were dried at room temperature for 7 days. The seeds were sowed in 26.5×51 cm germination disks, and 200 mg of $T_1$ seeds (about 10000 seeds) were accepted per disk, wherein the seeds had been previously suspended in 40 mL of 0.1% (w/v) agarose solution and stored at 4° C. for 2 days to complete the need for dormancy, in order to ensure synchronous seed germination.

Vermiculite was mixed with horse manure soil, the mixture was sub-irrigated with water to wet same, and water was drained by gravity. The pretreated seeds (each 40 mL) were sowed evenly in the soil mixture using a pipette, and covered with a moisturizing cover for 4-5 days. The cover was removed 1 day before the step of performing the initial transformant selection by spraying glufosinate (used to select the co-transformed PAT gene) post emergence.

The $T_1$ plants were sprayed with a 0.2% solution of a Liberty herbicide (200 g ai/L of glufosinate) by a DeVilbiss compressed air nozzle at a spray volume of 10 mL/disk (703 L/ha) at 7 days after planting (DAP) and 11 DAP (the cotyledon stage and 2-4 leaf stage, respectively), to provide an effective amount of glufosinate of 280 g ai/ha per application. Surviving plants (actively growing plants) were identified 4-7 days after the final spraying, and transplanted to 7 cm×7 cm square pots prepared with horse manure soil and vermiculite (3-5 plants/disk). The transplanted plants were covered with a moisturizing cover for 3-4 days, and placed in a 22° C. culture chamber or directly transferred into a greenhouse as described above. Then, the cover was removed, and at least 1 day before testing the ability of the SUM1 gene to provide sulfonylurea herbicide tolerance, the plants were planted in a greenhouse (22±5° C., 50±30% RH, 14 hours of light: 10 hours of darkness, a minimum of 500 $\mu E/m^2 s^1$ natural+supplemental light).

Example 4. Detection of Herbicide Tolerance Effects of the Transgenic *Arabidopsis thaliana* Plants T1 transformants were initially selected from the untransformed seeds using a glufosinate selection scheme. About 40000 T1 seeds were screened, and 380 T1 positive transformants (PAT gene) were identified, with a transformation efficiency of about 0.95%. The tolerance to sulfonylurea herbicides were determined for *Arabidopsis thaliana* T1 plants into which the SUM1-01 nucleotide sequence was introduced, *Arabidopsis thaliana* T1 plants into which the control sequence 1 was introduced, *Arabidopsis thaliana* T1 plants into which the control sequence 2 was introduced, and wild-type *Arabidopsis thaliana* plants (18 days after sowing).

The *Arabidopsis thaliana* T1 plants into which the SUM1-01 nucleotide sequence was introduced, *Arabidopsis thaliana* T1 plants into which the control sequence 1 was introduced, *Arabidopsis thaliana* T1 plants into which the control sequence 2 was introduced, and wild-type *Arabidopsis thaliana* plants were sprayed with tribenuron-methyl (18 g ai/ha, one-fold field concentration), sulfometuron methyl (30 g ai/ha, one-fold field concentration), halosulfuron-methyl (34 g ai/ha, one-fold field concentration), pyrazosulfuron-ethyl (25 g ai/ha, one-fold field concentration), thifensulfuron (30 g ai/ha, one-fold field concentration), bensulfuron-methyl (30 g ai/ha, one-fold field concentration), metsulfuron-methyl (7.5 g ai/ha, one-fold field concentration), ethametsulfuron-methyl (15 g ai/ha, one-fold field concentration), chlorimuron-ethyl (15 g ai/ha, one-fold field concentration) or a blank solvent (water). Plants were detected for the resistance situations 14 days after spraying: those having a consistent growth status with the blank solvent (water) group after 14 days were classified as highly resistant plants, those having a bolting height less than ½ of that of the blank solvent (water) group after 14 days were classified as moderately resistant plants, those still not capable of bolting after 14 days were classified as poorly resistant plants, and those which were dead after 14 days were classified as non-resistant plants. Since each *Arabidopsis thaliana* T1 plant was an independent transformation event, a significant difference in individual T1 responses could be expected at a given dose. The results are as shown in Table 1 and FIG. 4.

TABLE 1

Experimental results of the tolerance of transgenic *Arabidopsis thaliana* T1 plants to sulfonylurea herbicides

| Treatment | *Arabidopsis thaliana* genotypes | Highly resistant | Moderately resistant | Poorly resistant | Non-resistant | Total |
|---|---|---|---|---|---|---|
| Blank solvent (water) | SUM1-01 | 31 | 0 | 0 | 0 | 31 |
| | Control sequence 1 | 29 | 0 | 0 | 0 | 29 |
| | Control sequence 2 | 30 | 0 | 0 | 0 | 30 |
| | Wild-type | 31 | 0 | 0 | 0 | 31 |
| 18 g ai/ha tribenuron-methyl (1xTri.) | SUM1-01 | 26 | 4 | 1 | 1 | 32 |
| | Control sequence 1 | 12 | 7 | 5 | 4 | 28 |
| | Control sequence 2 | 11 | 9 | 4 | 6 | 30 |
| | Wild-type | 0 | 0 | 0 | 32 | 32 |
| 30 g ai/ha sulfometuron-methyl (1xSul.) | SUM1-01 | 24 | 5 | 2 | 1 | 32 |
| | Control sequence 1 | 10 | 9 | 6 | 2 | 27 |
| | Control sequence 2 | 11 | 7 | 5 | 6 | 29 |
| | Wild-type | 0 | 0 | 0 | 31 | 31 |
| 34 g ai/ha halosulfuron-methyl (1xHal.) | SUM1-01 | 17 | 2 | 5 | 7 | 31 |
| | Control sequence 1 | 8 | 9 | 8 | 6 | 31 |
| | Control sequence 2 | 9 | 7 | 6 | 6 | 28 |
| | Wild-type | 0 | 0 | 0 | 32 | 32 |

TABLE 1-continued

Experimental results of the tolerance of transgenic *Arabidopsis thaliana* T1 plants to sulfonylurea herbicides

| Treatment | *Arabidopsis thaliana* genotypes | Highly resistant | Moderately resistant | Poorly resistant | Non-resistant | Total |
|---|---|---|---|---|---|---|
| 25 g ai/ha | SUM1-01 | 12 | 6 | 5 | 5 | 28 |
| pyrazosulfuron-ethyl | Control sequence 1 | 5 | 7 | 6 | 11 | 29 |
| (1xPyr.) | Control sequence 2 | 4 | 8 | 10 | 10 | 32 |
| | Wild-type | 0 | 0 | 0 | 32 | 32 |
| 30 g ai/ha | SUM1-01 | 28 | 0 | 0 | 3 | 31 |
| thifensulfuron | Control sequence 1 | 15 | 4 | 5 | 6 | 30 |
| (1xThi.) | Control sequence 2 | 16 | 2 | 5 | 6 | 29 |
| | Wild-type | 0 | 0 | 0 | 31 | 31 |
| 30 g ai/ha | SUM1-01 | 28 | 1 | 0 | 1 | 30 |
| bensulfuron-methy | Control sequence 1 | 16 | 5 | 4 | 5 | 30 |
| (1xBen.) | Control sequence 2 | 14 | 5 | 6 | 4 | 29 |
| | Wild-type | 0 | 0 | 0 | 30 | 30 |
| 7.5 g ai/ha | SUM1-01 | 18 | 4 | 5 | 5 | 32 |
| metsulfuron-methyl | Control sequence 1 | 9 | 5 | 8 | 6 | 28 |
| (1xMet.) | Control sequence 2 | 10 | 8 | 5 | 6 | 29 |
| | Wild-type | 0 | 0 | 0 | 32 | 32 |
| 15 g ai/ha | SUM1-01 | 24 | 2 | 0 | 6 | 32 |
| ethametsulfuron-methyl | Control sequence 1 | 15 | 4 | 5 | 7 | 31 |
| (1xEth.) | Control sequence 2 | 14 | 2 | 8 | 6 | 30 |
| | Wild-type | 0 | 0 | 0 | 32 | 32 |
| 15 g ai/ha | SUM1-01 | 23 | 2 | 4 | 3 | 32 |
| chlorimuron-ethyl | Control sequence 1 | 13 | 6 | 5 | 4 | 28 |
| (1xChl.) | Control sequence 2 | 14 | 7 | 5 | 3 | 29 |
| | Wild-type | 0 | 0 | 0 | 32 | 32 |

Figures 2, 4:
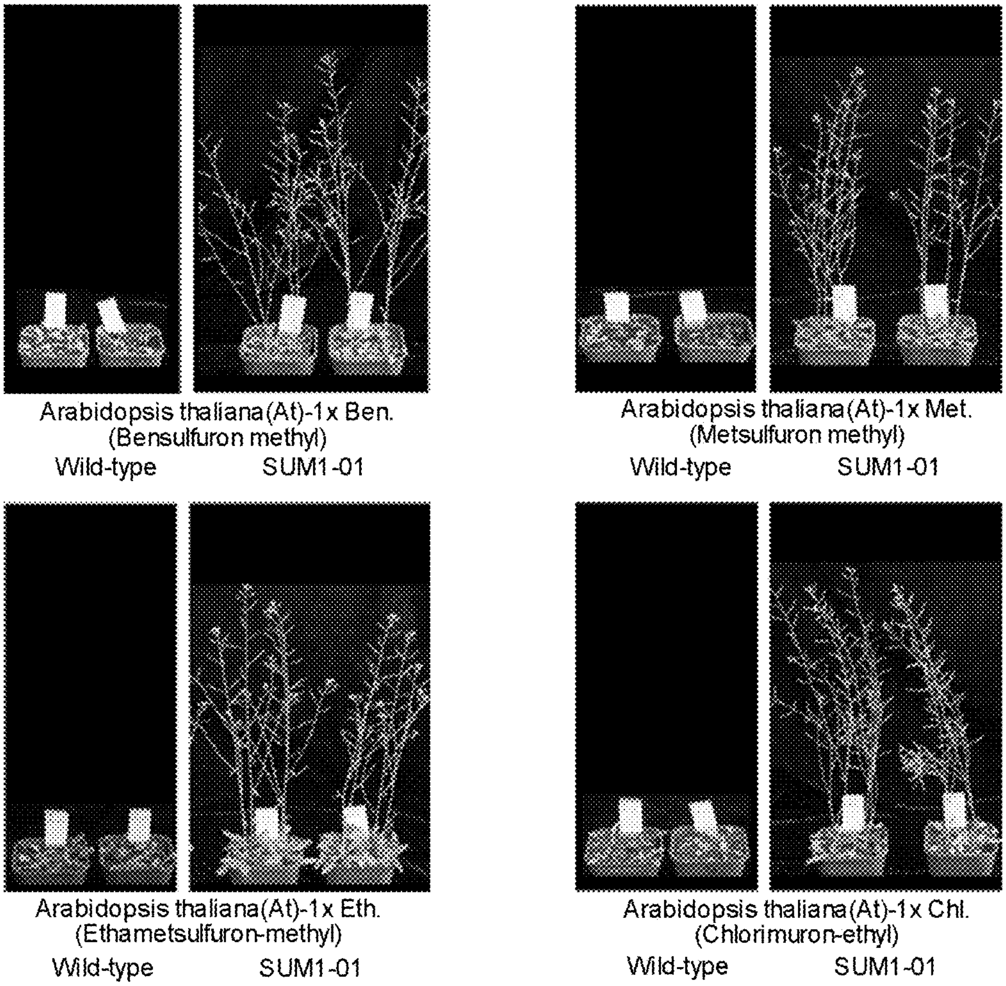

For *Arabidopsis thaliana*, one-fold field concentration of a sulfonylurea herbicide is an effective dose distinguishing sensitive plants from plants having an average level of resistance. The results of Table 1 and FIG. 4 show that: the herbicide tolerant protein SUM1 imparted sulfonylurea herbicide tolerance to individual *Arabidopsis thaliana* plants (there were individual plants having no tolerance because the insertion sites in the T1 generation plants were random, and there were differences in the expression levels of the tolerant gene which exhibited differences in the levels of the tolerance); for any of the sulfonylurea herbicides, compared with the *Arabidopsis thaliana* T1 plants into which the control sequence 1 was introduced and the *Arabidopsis thaliana* T1 plants into which the control sequence 2 was introduced, the *Arabidopsis thaliana* T1 plants into which SUM1-01 nucleotide sequence was introduced had a significantly increased tolerance to sulfonylurea herbicides; while the wild-type *Arabidopsis thaliana* plants had no tolerance to sulfonylurea herbicides.

Figure 5:
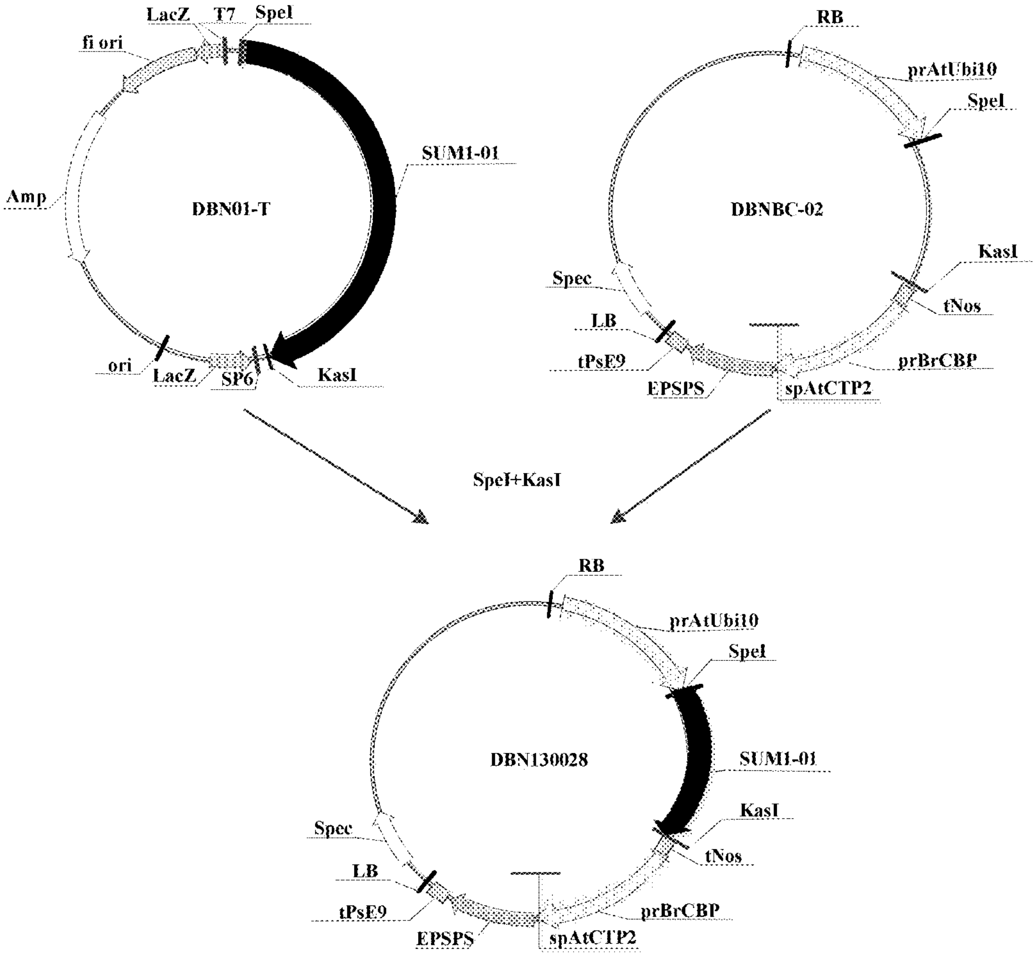
FIG. 5 is a construction flow chart of a recombinant expression vector DBN130028 containing a SUM1 nucleotide sequence for the herbicide tolerant protein, the coding gene thereof and a use thereof in the present invention.

Example 5. Construction of Recombinant Expression Vectors for Soybean and Transformation of *Agrobacterium* with the Recombinant Expression Vectors 1. Construction of Recombinant Expression Vectors Containing SUM1 Nucleotide Sequences for Soybean The recombinant cloning vector DBN01-T and an expression vector DBNBC-02 (vector backbone: pCAMBIA2301 (which can be provided by the CAMBIA institution)) were both digested with restriction enzymes SpeI and KasI; the excised SUM1-01 nucleotide sequence fragment was inserted between the SpeI and KasI sites in the expression vector DBNBC-02; and it is well known to a person skilled in the art to construct a vector using conventional enzyme digestion methods, wherein a recombinant expression vector DBN130028 was constructed, and the construction process of which was shown as FIG. 5 (Spec: the spectinomycin gene; RB: the right boundary; prAtUbi10: the *Arabidopsis thaliana* Ubiquitin 10 gene promoter (SEQ ID NO: 4); SUM1-01: the SUM1-01 nucleotide sequence (SEQ ID NO: 2); tNos: the terminator of a nopaline synthase gene (SEQ ID NO:5); prBrCBP: the rape eukaryotic elongation factor gene 1α (Tsf1) promoter (SEQ ID NO: 11); spAtCTP2: the *Arabidopsis thaliana* chloroplast transit peptide (SEQ ID NO: 12); EPSPS: the 5-enolpyruvylshikimate-3-phosphate synthase gene (SEQ ID NO: 13); tPsE9: the pea RbcS gene terminator (SEQ ID NO: 14); LB: the left boundary).

According to the method in point 2 of Example 2, *Escherichia coli* T1 competent cells were transformed with the recombinant expression vector DBN130028 using the heat shock method, and the plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant expression vector DBN130028 was the nucleotide sequence as shown in SEQ ID NO: 2 in the sequence listings, i.e., the SUM1-01 nucleotide sequence.

Figure 6:
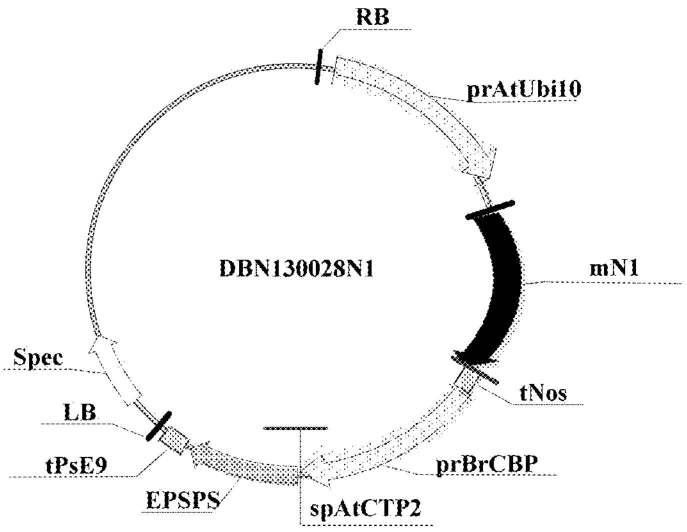
FIG. 6 is a schematic structural diagram of a recombinant expression vector DBN130028N1 containing a control sequence 1 for the herbicide tolerant protein, the coding gene thereof and a use thereof in the present invention.

2. Construction of Recombinant Expression Vectors Containing Control Sequences for Soybean The recombinant expression vector DBN130028N1 containing control sequence 1 was constructed using control sequence 1, according to the method for constructing the recombinant expression vector DBN130028 containing the SUM1 nucleotide sequence as described in point 1 of this example, and has a structure as shown in FIG. 6 (vector backbone: pCAMBIA2301 (which can be provided by the CAMBIA institution); Spec: the spectinomycin gene; RB: the right boundary; prAtUbi10: the *Arabidopsis thaliana* Ubiquitin 10 gene promoter (SEQ ID NO: 4); mN1: control sequence 1 (SEQ ID NO: 9); tNos: the terminator of a nopaline synthase gene (SEQ ID NO:5); prBrCBP: the rape eukaryotic elongation factor gene 1α (Tsf1) promoter (SEQ ID NO: 11); spAtCTP2: the *Arabidopsis thaliana* chloroplast transit peptide (SEQ ID NO: 12); EPSPS: the 5-enolpyruvylshikimate-3-phosphate synthase gene (SEQ ID NO: 13); tPsE9: the pea RbcS gene terminator (SEQ ID NO: 14); LB: the left boundary). Positive clones were validated by sequencing, with the results showing that the control sequence 1 inserted into the recombinant expression vector DBN130028N1 was the nucleotide sequence as shown in SEQ ID NO: 9 in the sequence listings, i.e., the control sequence 1 was inserted correctly.

The recombinant expression vector DBN130028N2 containing control sequence 2 was constructed using the control sequence 2 according to the method for constructing the recombinant expression vector DBN130028N1 containing control sequence 1 as described above. Positive clones were validated by sequencing, with the results showing that the control sequence 2 inserted into the recombinant expression vector DBN130028N2 was the nucleotide sequence as shown in SEQ ID NO: 10 in the sequence listings, i.e., the control sequence 2 was inserted correctly.

3. Transformation of *Agrobacterium* with the Recombinant Expression Vectors

*Agrobacterium* LBA4404 (Invitrogen, Chicago, USA, CAT: 18313-015) was transformed with the recombinant expression vectors DBN130028, DBN130028N1 and DBN130028N2 which have been constructed correctly using a liquid nitrogen method, under the following transformation conditions: placing 100 μL of *Agrobacterium* LBA4404, and 3 μL of plasmid DNA (recombinant expression vector) in liquid nitrogen for 10 minutes, and warm water bathing at 37° C. for 10 minutes; inoculating the transformed *Agrobacterium* LBA4404 into an LB tube, culturing under the conditions of a temperature of 28° C. and a rotation speed of 200 rpm for 2 hours, spreading on an LB plate containing 50 mg/L of rifampicin and 50 mg/L of spectinomycin until positive single clones were grown, picking out single clones for culturing and extracting the plasmids thereof, and performing enzyme digestion verification using restriction enzymes. The results showed that the structures of the recombinant expression vectors DBN130028, DBN130028N1 and DBN130028N2 were completely correct.

Example 6. Acquisition and Verification of Transgenic Soybean Plants

1. Acquisition of Transgenic Soybean Plants

According to the *Agrobacterium* infection method conventionally used, the cotyledonary node tissue of sterilely cultured soybean variety Zhonghuang13 was co-cultured with the *Agrobacterium* in point 3 of Example 5, so as to introduce the T-DNA (including the *Arabidopsis thaliana* Ubiquitin10 gene promoter sequence, an SUM1-01 nucleotide sequence, a control sequence 1, a control sequence 2, the tNos terminator, the rape eukaryotic elongation factor gene 1α promoter, the *Arabidopsis thaliana* chloroplast transit peptide, a 5-enolpyruvylshikimate-3-phosphate synthase gene, and the pea RbcS gene terminator) in the recombinant expression vectors DBN130028, DBN130028N1 and DBN130028N2 constructed in points 1 and 2 of Example 5 into the soybean chromosomes, and thereby obtaining soybean plants into which the SUM1-01 nucleotide sequence was introduced, soybean plants into which the control sequence 1 was introduced and soybean plants into which the control sequence 2 was introduced; meanwhile, wild-type soybean plants were used as the control.

As regards the *Agrobacterium*-mediated soybean transformation, briefly, mature soybean seeds were germinated in a soybean germination culture medium (3.1 g/L of B5 salt, B5 vitamin, 20 g/L of sucrose, and 8 g/L of agar, with a pH of 5.6), and the seeds were inoculated on a germination culture medium and cultured under the conditions of a temperature of 25±1° C.; and a photoperiod (light/dark) of 16 h/8 h. After 4-6 days of germination, soybean sterile seedlings swelling at bright green cotyledonary nodes were taken, hypocotyledonary axes were cut off 3-4 millimeters below the cotyledonary nodes, the cotyledons were cut longitudinally, and apical buds, lateral buds and seminal roots were removed. A wound was made at a cotyledonary node using the knife back of a scalpel, and the wounded cotyledonary node tissues were contacted with an *Agrobacterium* suspension, wherein the *Agrobacterium* can transfer the SUM1-01 nucleotide sequence to the wounded cotyledonary node tissues (step 1: the infection step). In this step, the cotyledonary node tissues were preferably immersed in the *Agrobacterium* suspension (OD660=0.5-0.8, an infection culture medium (2.15 g/L of MS salt, B5 vitamin, 20 g/L of sucrose, 10 g/L of glucose, 40 mg/L of acetosyringone (AS), 4 g/L of 2-morpholine ethanesulfonic acid (MES), and 2 mg/L of zeatin (ZT), pH 5.3)) to initiate the inoculation. The cotyledonary node tissues were co-cultured with *Agrobacterium* for a period of time (3 days) (step 2: the co-culturing step). Preferably, the cotyledonary node tissues were cultured in a solid culture medium (4.3 g/L of MS salt, B5 vitamin, 20 g/L of sucrose, 10 g/L of glucose, 4 g/L of 2-morpholine ethanesulfonic acid (MES), 2 mg/L of zeatin, and 8 g/L of agar, with a pH of 5.6) after the infection step. After this co-culturing stage, there can be an optional "recovery" step. In the "recovery" step, there may be at least one antibiotic (cephalosporin) known to inhibit the growth of *Agrobacterium* in a recovery culture medium (3.1 g/L of B5 salt, B5 vitamin, 1 g/L of 2-morpholine ethanesulfonic acid (MES), 30 g/L of sucrose, 2 mg/L of zeatin (ZT), 8 g/L of agar, 150 mg/L of cephalosporin, 100 mg/L of glutamic acid, and 100 mg/L of aspartic acid, with a pH of 5.6), without the addition of a selective agent for a plant transformant (step 3: the recovery step). Preferably, tissue blocks regenerated from the cotyledonary nodes were cultured in a solid culture medium with an antibiotic, but without a selective agent, to eliminate *Agrobacterium* and provide a recovery stage for the infected cells. Subsequently, the tissue blocks regenerated from the cotyledonary nodes were cultured in a culture medium containing a selective agent (glyphosate), and growing transformed calli were selected (step 4: the selection step). Preferably, the tissue blocks regenerated from the cotyledonary nodes were cultured in a screening solid culture medium (3.1 g/L of B5 salt, B5 vitamin, 1 g/L of 2-morpholine ethanesulfonic acid (MES), 30 g/L of sucrose, 1 mg/L of 6-benzyladenine (6-BAP), 8 g/L of agar, 150 mg/L of cephalosporin, 100 mg/L of glutamic acid, 100 mg/L of aspartic acid, and 0.25 mol/L of N-(phosphonomethyl)glycine, with a pH of 5.6) containing a selective agent, thus resulting in selective growth of the transformed cells. Then, plants were regenerated from the transformed cells (step 5: the regeneration step). Preferably, the tissue blocks regenerated from the cotyledonary nodes grown in a culture medium containing a selective agent were cultured in solid culture media (a B5 differentiation culture medium and B5 rooting culture medium) to regenerate plants.

The screened out resistant tissues were transferred onto the B5 differentiation culture medium (3.1 g/L of B5 salt, B5 vitamin, 1 g/L of 2-morpholine ethanesulfonic acid (MES), 30 g/L of sucrose, 1 mg/L of zeatin (ZT), 8 g/L of agar, 150 mg/L of cephalosporin, 50 mg/L of glutamic acid, 50 mg/L of aspartic acid, 1 mg/L of gibberellin, 1 mg/L of auxin, and 0.25 mol/L of N-(phosphonomethyl)glycine, with a pH of 5.6), and cultured at 25° C. for differentiation. The differentiated seedlings were transferred onto the B5 rooting culture medium (3.1 g/L of B5 salt, B5 vitamin, 1 g/L of 2-morpholine ethanesulfonic acid (MES), 30 g/L of sucrose, 8 g/L of agar, 150 mg/L of cephalosporin, and 1 mg/L of indole-3-butyric acid (IBA)), cultured in the rooting culture medium until reaching a height of about 10 cm at 25° C., and transferred to a glasshouse for culturing until fruiting. In the greenhouse, the plants were cultured at 26° C. for 16 hours, and then cultured at 20° C. for 8 hours every day.

2. Verification of the Transgenic Soybean Plants Using TaqMan

About 100 mg of leaves from the soybean plants into which the SUM1-01 nucleotide sequence was introduced, soybean plants into which the control sequence 1 was introduced and soybean plants into which the control sequence 2 was introduced were taken as samples, and the genomic DNA thereof was extracted with a DNeasy Plant Maxi Kit of Qiagen, and copy numbers of an EPSPS gene were detected by the Taqman probe fluorescence quantitative PCR method so as to determine the copy numbers of the SUM1 gene. At the same time, wild-type soybean plants were used as controls, and detected and analyzed according to the above-mentioned method. Triple repeats were set for the experiments, and were averaged.

The specific method for detecting the copy number of the EPSPS gene was as follows:

Step 11. 100 mg of leaves of the soybean plants into which the SUM1-01 nucleotide sequence was introduced, soybean plants into which the control sequence 1 was introduced, soybean plants into which the control sequence 2 was introduced or wild-type soybean plants was taken, and ground into a homogenate using liquid nitrogen in a mortar, and triple repeats were taken for each sample;

Step 12. The genomic DNA of the above-mentioned samples was extracted using a DNeasy Plant Mini Kit of Qiagen, and the particular method refers to the product manual thereof;

Step 13. The concentrations of the genomic DNA of the above-mentioned samples were detected using NanoDrop 2000 (Thermo Scientific);

Step 14. The concentrations of the genomic DNA of the above-mentioned samples were adjusted to a consistent concentration value which ranges from 80 to 100 ng/μL;

Step 15. The copy numbers of the samples were identified using the Taqman probe fluorescence quantitative PCR method, wherein samples for which the copy numbers had been identified and known were taken as standards, the samples of the wild-type soybean plants were taken as the control, and triple repeats were taken for each sample, and were averaged; the sequences of fluorescence quantitative PCR primers and a probe were as follows:

the following primers and probe were used to detect the EPSPS gene sequence:

primer 1: CTGGAAGGCGAGGACGTCATCAATA, as shown in SEQ ID NO: 15 in the sequence listings;

primer 2: TGGCGGCATTGCCGAAATCGAG, as shown in SEQ ID NO: 16 in the sequence listings;

probe 1: ATGCAGGCGATGGGCGCCCGCATCCGTA, as shown in SEQ ID NO: 17 in the sequence listings;

PCR Reaction System:

| | |
|---|---|
| JumpStart ™ Taq ReadyMix ™ (Sigma) | 10 μL |
| 50x primer/probe mixture | 1 μL |
| genomic DNA | 3 μL |
| water ($ddH_2O$) | 6 μL |

The 50× primer/probe mixture comprises 45 μL of each primer at a concentration of 1 mM, 50 μL of the probe at a concentration of 100 μM, and 860 μL of 1×TE buffer, and was stored at 4° C. in an amber tube.

PCR Reaction Conditions:

| Step | Temperature | Time |
|---|---|---|
| 21 | 95° C. | 5 minute |
| 22 | 95° C. | 30 seconds |
| 23 | 60° C. | 1 minute |
| 24 | back to step 22, repeated 40 times | |

Data was analyzed using software SDS2.3 (Applied Biosystems).

It was further demonstrated, by analyzing the experimental results of the copy number of the EPSPS gene, that the SUM1-01 nucleotide sequence, control sequence 1 and control sequence 2 had all been incorporated into the chromosome of the detected soybean plants, and all of the soybean plants into which the SUM1-01 nucleotide sequence was introduced, the soybean plants into which the control sequence 1 was introduced, and the soybean plants into which the control sequence 2 was introduced resulted in single-copy transgenic soybean plants.

Example 7. Detection of Herbicide Tolerance Effects of the Transgenic Soybean Plants The tolerance of the soybean plants into which the SUM1-01 nucleotide sequence was introduced, the soybean plants into which the control sequence 1 was introduced, the soybean plants into which the control sequence 2 was introduced and the wild-type soybean plants (at seedling stage) to sulfonylurea herbicides were detected.

The soybean plants into which the SUM1-01 nucleotide sequence was introduced, the soybean plants into which the control sequence 1 was introduced, the soybean plants into which the control sequence 2 was introduced and the wild-type soybean plants were taken and sprayed with tribenuron-methyl (72 g ai/ha, four-fold field concentration), sulfometuron methyl (120 g ai/ha, four-fold field concentration), halosulfuron-methyl (34 g ai/ha, one-fold field concentration), pyrazosulfuron-ethyl (25 g ai/ha, one-fold field concentration), thifensulfuron (120 g ai/ha, four-fold field concentration), bensulfuron-methyl (120 g ai/ha, four-fold field concentration), metsulfuron-methyl (30 g ai/ha, four-fold field concentration), ethametsulfuron-methyl (60 g ai/ha, four-fold field concentration), chlorimuron-ethyl (60 g ai/ha, four-fold field concentration) or a blank solvent (water). The degree of damage caused by the herbicide was measured for each plant according to the leaf curl degree and the growth point damage degree 3 days after spraying (3 DAT), 7 days after spraying (7 DAT), 14 days after spraying (14 DAT) and 21 days after spraying (21 DAT): the case where the leaves are flat as untreated plants and the growth points are intact is defined as having a damage degree of 0%; the case where veins are locally browned, new leaves are malformed and plant growth is slow is defined as having a damage degree of 50%; and the case where veins are purple, the whole plant is dead and the growth points are browned and dry is defined as having a damage degree of 100%. The soybean plants into which the SUM1-01 nucleotide sequence was introduced were of two strains in total (S1 and S2), the soybean plants into which the control sequence 1 was introduced were of two strains in total (S3 and S4), the soybean plants into which the control sequence 2 was introduced were of two strains in total (S5 and S6), and the wild-type soybean plants were of one strain in total (CK1); and 10-15 plants were selected from each strain and tested. The results are as shown in Table 2.

TABLE 2

Experimental results of the herbicide tolerance of transgenic soybean T1 plants

| Treatment | Soybean genotypes | Average damage % 3DAT | Average damage % 7DAT | Average damage % 14DAT | Average damage % 21DAT |
|---|---|---|---|---|---|
| Blank solvent (water) | S1 | 0 | 0 | 0 | 0 |
| | S2 | 0 | 0 | 0 | 0 |
| | S3 | 0 | 0 | 0 | 0 |
| | S4 | 0 | 0 | 0 | 0 |
| | S5 | 0 | 0 | 0 | 0 |
| | S6 | 0 | 0 | 0 | 0 |
| | CK1 | 0 | 0 | 0 | 0 |
| 72 g ai/ha tribenuron-methyl (4xTri.) | S1 | 0 | 0 | 0 | 0 |
| | S2 | 0 | 0 | 0 | 0 |
| | S3 | 15 | 25 | 23 | 20 |
| | S4 | 14 | 22 | 24 | 19 |
| | S5 | 16 | 24 | 25 | 20 |
| | S6 | 15 | 25 | 25 | 21 |
| | CK1 | 43 | 83 | 100 | 100 |
| 120 g ai/ha sulfometuron-methyl (4xSul.) | S1 | 0 | 0 | 0 | 0 |
| | S2 | 0 | 0 | 0 | 0 |
| | S3 | 18 | 26 | 23 | 22 |
| | S4 | 17 | 25 | 22 | 20 |
| | S5 | 16 | 27 | 24 | 21 |
| | S6 | 17 | 26 | 25 | 22 |
| | CK1 | 43 | 81 | 100 | 100 |
| 34 g ai/ha halosulfuron-methyl (1xHal.) | S1 | 13 | 0 | 0 | 0 |
| | S2 | 15 | 0 | 0 | 0 |
| | S3 | 26 | 31 | 25 | 22 |
| | S4 | 27 | 33 | 26 | 23 |
| | S5 | 25 | 30 | 25 | 22 |
| | S6 | 26 | 34 | 27 | 25 |
| | CK1 | 47 | 81 | 100 | 100 |
| 25 g ai/ha pyrazosulfuron-ethyl (1x Pyr.) | S1 | 17 | 15 | 0 | 0 |
| | S2 | 18 | 16 | 0 | 0 |
| | S3 | 24 | 29 | 25 | 12 |
| | S4 | 22 | 27 | 25 | 12 |
| | S5 | 23 | 27 | 26 | 13 |
| | S6 | 20 | 28 | 24 | 12 |
| | CK1 | 47 | 83 | 100 | 100 |
| 120 g ai/ha thifensulfuron (4xThi.) | S1 | 0 | 0 | 0 | 0 |
| | S2 | 0 | 0 | 0 | 0 |
| | S3 | 18 | 20 | 16 | 13 |
| | S4 | 17 | 19 | 16 | 10 |
| | S5 | 17 | 19 | 15 | 10 |
| | S6 | 16 | 20 | 16 | 12 |
| | CK1 | 28 | 71 | 100 | 100 |

TABLE 2-continued

Experimental results of the herbicide tolerance of transgenic soybean T1 plants

| Treatment | Soybean genotypes | Average damage % 3DAT | Average damage % 7DAT | Average damage % 14DAT | Average damage % 21DAT |
|---|---|---|---|---|---|
| 120 g ai/ha bensulfuron-methy (4xBen.) | S1 | 0 | 0 | 0 | 0 |
| | S2 | 0 | 0 | 0 | 0 |
| | S3 | 18 | 20 | 17 | 14 |
| | S4 | 17 | 21 | 16 | 13 |
| | S5 | 19 | 22 | 16 | 12 |
| | S6 | 18 | 21 | 16 | 13 |
| | CK1 | 35 | 78 | 100 | 100 |
| 30 g ai/ha metsulfuron-methyl (4xMet.) | S1 | 11 | 0 | 0 | 0 |
| | S2 | 10 | 0 | 0 | 0 |
| | S3 | 23 | 25 | 22 | 19 |
| | S4 | 24 | 26 | 23 | 19 |
| | S5 | 22 | 26 | 23 | 19 |
| | S6 | 23 | 25 | 23 | 18 |
| | CK1 | 47 | 85 | 100 | 100 |
| 60 g ai/ha ethametsulfuron-methyl (4xEth.) | S1 | 9 | 0 | 0 | 0 |
| | S2 | 6 | 0 | 0 | 0 |
| | S3 | 18 | 22 | 20 | 18 |
| | S4 | 20 | 23 | 21 | 17 |
| | S5 | 20 | 23 | 21 | 17 |
| | S6 | 21 | 24 | 22 | 18 |
| | CK1 | 43 | 82 | 100 | 100 |
| 60 g ai/ha chlorimuron-ethyl (4xChl.) | S1 | 9 | 0 | 0 | 0 |
| | S2 | 8 | 0 | 0 | 0 |
| | S3 | 11 | 15 | 6 | 0 |
| | S4 | 10 | 14 | 5 | 0 |
| | S5 | 11 | 15 | 5 | 0 |
| | S6 | 12 | 16 | 6 | 0 |
| | CK1 | 20 | 60 | 55 | 50 |

For soybeans, four-fold field concentration of most sulfonylurea herbicides is an effective dose distinguishing sensitive plants from plants having an average level of resistance. The results in Table 2 showed that the herbicide tolerant protein SUM1 imparted transgenic soybean plants with the sulfonylurea herbicide tolerance; for any of the sulfonylurea herbicides, compared with the soybean plants into which the control sequence 1 was introduced and the soybean plants into which the control sequence 2 was introduced, the soybean plants into which the SUM1-01 nucleotide sequence was introduced had a significantly increased tolerance to sulfonylurea herbicides; while the wild-type soybean plants had no tolerance to most sulfonylurea herbicides.

Example 8. Construction of Recombinant Expression Vectors for Maize

Figure 7:
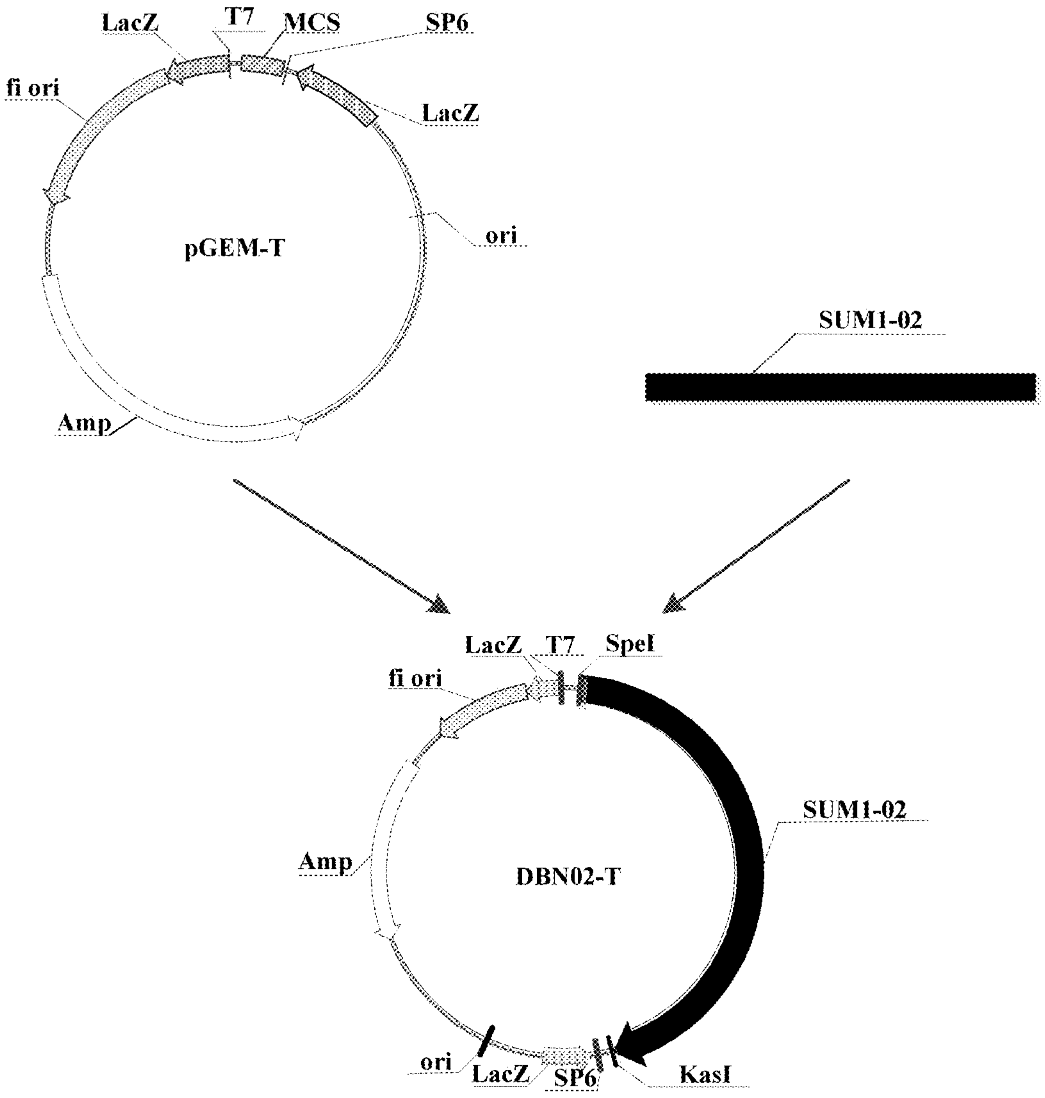
FIG. 7 is a construction flow chart of a recombinant cloning vector DBN02-T containing a SUM1 nucleotide sequence for the herbicide tolerant protein, the coding gene thereof and a use thereof in the present invention.

1. Construction of Recombinant Cloning Vectors Containing SUM1 Nucleotide Sequences for Maize The synthetic SUM1-02 nucleotide sequence was ligated into a cloning vector pGEM-T (Promega, Madison, USA, CAT: A3600), and the operational procedure was carried out according to Promega's pGEM-T vector product instructions, thereby obtaining a recombinant cloning vector DBN02-T, the construction process of which was as shown in FIG. 7 (wherein, Amp represents the ampicillin resistance gene; f1 represents the origin of replication of phage f1; LacZ is LacZ initiation codon; SP6 is SP6 RNA polymerase promoter; T7 is T7 RNA polymerase promoter; SUM1-02 is the SUM1-02 nucleotide sequence (SEQ ID NO: 3); and MCS is a multiple cloning site).

According to the method in point 1 of Example 2, *Escherichia coli* T1 competent cells were transformed with the recombinant cloning vector DBN01-T using the heat shock method, and the plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant cloning vector DBN02-T was the nucleotide sequence as shown in SEQ ID NO: 3 in the sequence listings, i.e., the SUM1-02 nucleotide sequence.

Figure 8:
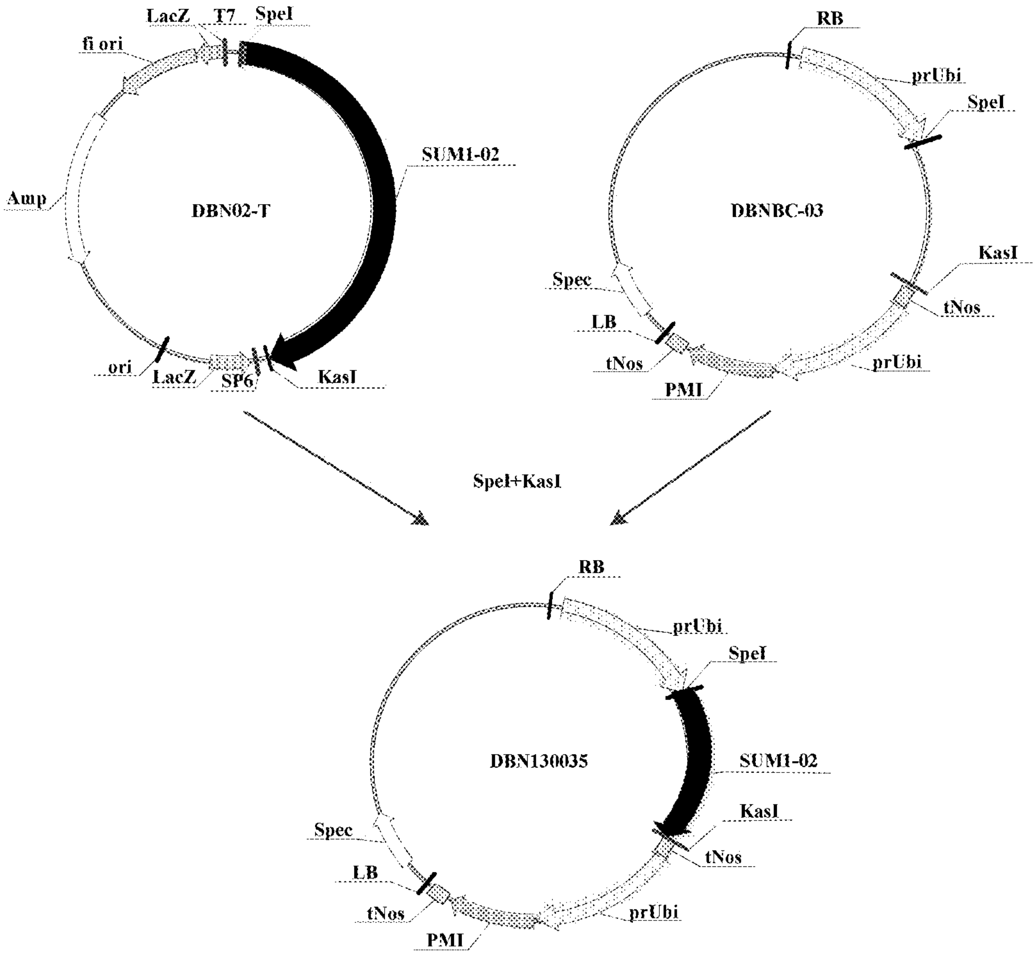
FIG. 8 is a construction flow chart of a recombinant expression vector DBN130035 containing a SUM1 nucleotide sequence for the herbicide tolerant protein, the coding gene thereof and a use thereof in the present invention.

2. Construction of Recombinant Expression Vectors Containing SUM1 Nucleotide Sequences for Maize The recombinant cloning vector DBN02-T and an expression vector DBNBC-03 (vector backbone: pCAMBIA2301 (which can be provided by the CAMBIA institution)) were both digested with restriction enzymes SpeI and KasI; the excised SUM1-02 nucleotide sequence fragment was inserted between the SpeI and KasI sites in the expression vector DBNBC-03; and it is well known to a person skilled in the art to construct a vector using conventional enzyme digestion methods, wherein a recombinant expression vector DBN130035 was constructed, and the construction process of which was shown as FIG. 8 (Spec: the spectinomycin gene; RB: the right boundary; prUbi: the maize Ubiquitin 1 gene promoter (SEQ ID NO: 18); SUM1-02: the SUM1-02 nucleotide sequence (SEQ ID NO: 3); tNos: the terminator of a nopaline synthase gene (SEQ ID NO:5); PMI: the phosphomannose isomerase gene (SEQ ID NO: 19); LB: the left boundary).

According to the method in point 2 of Example 2, *Escherichia coli* T1 competent cells were transformed with the recombinant expression vector DBN130035 using the heat shock method, and the plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant expression vector DBN130035 was the nucleotide sequence as shown in SEQ ID NO: 3 in the sequence listings, i.e., the SUM1-02 nucleotide sequence.

Figure 9:
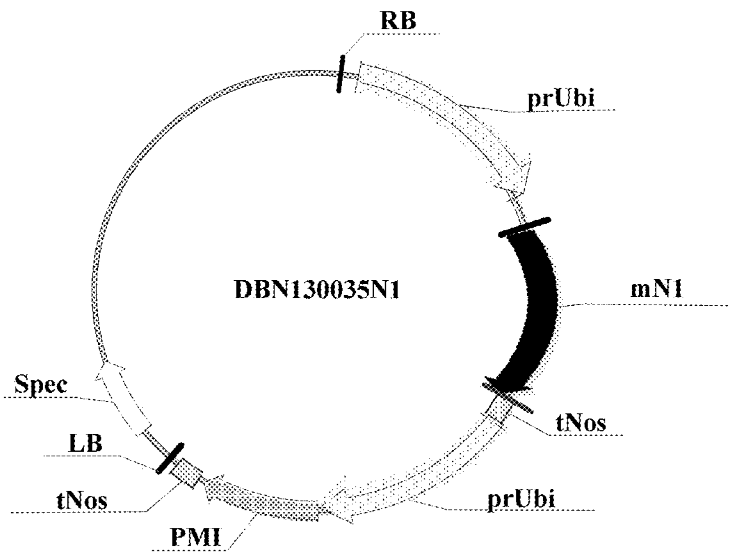
FIG. 9 is a schematic structural diagram of a recombinant expression vector DBN130035N1 containing a control sequence 1 for the herbicide tolerant protein, the coding gene thereof and a use thereof in the present invention.

3. Construction of Recombinant Expression Vectors Containing Control Sequences for Maize The recombinant expression vector DBN130035N1 containing control sequence 1 was constructed using control sequence 1, according to the method for constructing the recombinant expression vector DBN130035 containing the SUM1 nucleotide sequence as described in point 2 of this example, and has a structure as shown in FIG. 9 (vector backbone: pCAMBIA2301 (which can be provided by the CAMBIA institution); Spec: the spectinomycin gene; RB: the right boundary; prUbi: the maize Ubiquitin 1 gene promoter (SEQ ID NO: 18); mN1: control sequence 1 (SEQ ID NO: 9); tNos: the terminator of a nopaline synthase gene (SEQ ID NO:5); PMI: the phosphomannose isomerase gene (SEQ ID NO: 19); LB: the left boundary). Positive clones were validated by sequencing, with the results showing that the control sequence 1 inserted into the recombinant expression vector DBN130035N1 was the nucleotide sequence as shown in SEQ ID NO: 9 in the sequence listings, i.e., the control sequence 1 was inserted correctly.

The recombinant expression vector DBN130035N2 containing control sequence 2 was constructed using the control sequence 2 according to the method for constructing the recombinant expression vector DBN130035N1 containing control sequence 1 as described above. Positive clones were validated by sequencing, with the results showing that the control sequence 2 inserted into the recombinant expression vector DBN130035N2 was the nucleotide sequence as shown in SEQ ID NO: 10 in the sequence listing, i.e., the control sequence 2 was inserted correctly.

4. Transformation of *Agrobacterium* with the Recombinant Expression Vectors for Maize

*Agrobacterium* LBA4404 (Invitrogen, Chicago, USA, CAT: 18313-015) was transformed with the recombinant expression vectors DBN130035, DBN130035N1 and DBN130035N2 which have been constructed correctly using a liquid nitrogen method, with the following transformation conditions: placing 100 μL of *Agrobacterium* LBA4404, and 3 μL of plasmid DNA (recombinant expression vector) in liquid nitrogen for 10 minutes, and warm water bathing at 37° C. for 10 minutes; inoculating the transformed *Agrobacterium* LBA4404 into an LB tube, culturing under the conditions of a temperature of 28° C. and a rotation speed of 200 rpm for 2 hours, spreading on an LB plate containing 50 mg/L of rifampicin and 50 mg/L of spectinomycin until positive single clones were grown, picking out single clones for culturing and extracting the plasmids thereof, and performing enzyme digestion verification using restriction enzymes. The results showed that the structures of the recombinant expression vectors DBN130035, DBN130035N1 and DBN130035N2 were completely correct.

Example 9. Acquisition and Verification of Transgenic Maize Plants

According to the conventionally used *Agrobacterium* infection method, young embryos of sterilely cultured maize variety Zong31 (Z31) were co-cultured with the *Agrobacterium* in point 4 of Example 8, so as to introduce T-DNA (including the maize Ubiquitin1 gene promoter sequence, the SUM1-02 nucleotide sequence, the control sequence 1, the control sequence 2, the PMI gene and the tNos terminator sequence) in the recombinant expression vectors DBN130035, DBN130035N1 and DBN130035N2 constructed in points 2 and 3 of Example 8 into the maize chromosome, thereby obtaining maize plants into which the SUM1-02 nucleotide sequence was introduced, maize plants into which the control sequence 1 was introduced and maize plants into which the control sequence 2 was introduced; meanwhile, wild-type maize plants were used as the control.

As regards the *Agrobacterium*-mediated maize transformation, briefly, immature young embryos were separated from maize, and contacted with an *Agrobacterium* suspension, wherein the *Agrobacterium* can transfer the SUM1-02 nucleotide sequence to at least one cell of one of the young embryos (step 1: the infection step). In this step, the young embryos were preferably immersed in an *Agrobacterium* suspension (OD660=0.4-0.6, an infection culture medium (4.3 g/L of MS salt, MS vitamin, 300 mg/L of casein, 68.5 g/L of sucrose, 36 g/L of glucose, 40 mg/L of acetosyringone (AS), and 1 mg/L of 2,4-dichlorphenoxyacetic acid (2,4-D), with a pH of 5.3)) to initiate the inoculation. The young embryos were co-cultured with *Agrobacterium* for a period of time (3 days) (step 2: the co-culturing step). Preferably, the young embryos were cultured in a solid culture medium (4.3 g/L of MS salt, MS vitamin, 300 mg/L of casein, 20 g/L of sucrose, 10 g/L of glucose, 100 mg/L of acetosyringone (AS), 1 mg/L of 2,4-dichlorphenoxyacetic acid (2,4-D), and 8 g/L of agar, with a pH of 5.8) after the infection step. After this co-culturing stage, there can be an optional "recovery" step. In the "recovery" step, there may be at least one antibiotic (cephalosporin) known to inhibit the growth of *Agrobacterium* in a recovery culture medium (4.3 g/L of MS salt, MS vitamin, 300 mg/L of casein, 30 g/L of sucrose, 1 mg/L of 2,4-dichlorphenoxyacetic acid (2,4-D), and 3 g/L of phytagel, with a pH of 5.8), without the addition of a selective agent for a plant transformant (step 3: the recovery step). Preferably, the young embryos were cultured in a solid culture medium with an antibiotic, but without a selective agent, in order to eliminate *Agrobacterium* and provide a recovery stage for the infected cells. Subsequently, the inoculated young embryos were cultured in a culture medium containing a selective agent (mannose), and growing transformed calli were selected (step 4: the selection step). Preferably, the young embryos were cultured in a screening solid culture medium (4.3 g/L of MS salt, MS vitamin, 300 mg/L of casein, 30 g/L of sucrose, 12.5 g/L of mannose, 1 mg/L of 2,4-dichlorphenoxyacetic acid (2,4-D), and 3 g/L of phytagel, with a pH of 5.8) with a selective agent, resulting in the selective growth of transformed cells. Then, plants were regenerated from the calli (step 5: the regeneration step). Preferably, the calli grown in a culture medium containing a selective agent were cultured in solid culture media (an MS differentiation culture medium and MS rooting culture medium) to regenerate plants.

Resistant calli which were screened out were transferred onto the MS differentiation culture medium (4.3 g/L of MS salt, MS vitamin, 300 mg/L of casein, 30 g/L of sucrose, 2 mg/L of 6-benzyladenine, 5 g/L of mannose, and 3 g/L of phytagel, with a pH of 5.8), and cultured at 25° C. for differentiation. The differentiated seedlings were transferred onto the MS rooting culture medium (2.15 g/L of MS salt, MS vitamin, 300 mg/L of casein, 30 g/L of sucrose, 1 mg/L of indole-3-acetic acid, and 3 g/L of phytagel, with a pH of 5.8), cultured at 25° C. to a height of about 10 cm, and transferred to a glasshouse for culturing until fruiting. In the greenhouse, the plants were cultured at 28° C. for 16 hours, and then cultured at 20° C. for 8 hours every day.

2. Verification of the Transgenic Maize Plants Using TaqMan

The maize plant into which the SUM1-02 nucleotide sequence was introduced, the maize plant into which the control sequence 1 was introduced and the maize plant into which the control sequence 2 was introduced were detected and analyzed according to the method for verifying transgenic soybean plants with TaqMan as described in point 2 of Example 6. The copy number of the PMI gene was detected by the Taqman probe fluorescence quantitative PCR method so as to determine the copy number of the SUM1 gene. Meanwhile, wild-type maize plants were used as the control, and detected and analyzed according to the above-mentioned method. Triple repeats were set for the experiments, and were averaged.

The following primers and probe were used to detect the PMI gene sequence:

primer 3: GCTGTAAGAGCTTACTGAAAAAATTAACA, as shown in SEQ ID NO: 20 in the sequence listings;

primer 4: CGATCTGCAGGTCGACGG, as shown in SEQ ID NO: 21 in the sequence listings;

probe 2: TCTCTTGCTAAGCTGGGAGCTCGATCC, as shown in SEQ ID NO: 22 in the sequence listings.

It was further demonstrated, by analyzing the experimental results of the copy number of PMI gene, that the SUM1-02 nucleotide sequence, control sequence 1 and control sequence 2 had all been incorporated into the chromosome of the detected maize plants, and all of the maize plants into which the SUM1-02 nucleotide sequence was introduced, the maize plants into which the control sequence 1 was introduced, and the maize plants into which the control sequence 2 was introduced resulted in single-copy transgenic maize plants.

Example 10. Detection of Herbicide Tolerance Effects of the Transgenic Maize Plants The tolerance of the maize plants into which the SUM1-02 nucleotide sequence was introduced, the maize plants into which the control sequence 1 was introduced, the maize plants into which the control sequence 2 was introduced and the wild-type maize plants (at V3-V4 stages) to sulfonylurea herbicides were detected.

The maize plants into which the SUM1-02 nucleotide sequence was introduced, the maize plants into which the control sequence 1 was introduced, the maize plants into which the control sequence 2 was introduced and the wild-type maize plants were taken and sprayed with tribenuron-methyl (72 g ai/ha, four-fold field concentration), sulfometuron methyl (120 g ai/ha, four-fold field concentration), halosulfuron-methyl (136 g ai/ha, four-fold field concentration), pyrazosulfuron-ethyl (100 g ai/ha, four-fold field concentration), thifensulfuron (120 g ai/ha, four-fold field concentration), bensulfuron-methyl (120 g ai/ha, four-fold field concentration), metsulfuron-methyl (30 g ai/ha, four-fold field concentration), ethametsulfuron-methyl (60 g ai/ha, four-fold field concentration), chlorimuron-ethyl (60 g ai/ha, four-fold field concentration) or a blank solvent (water). The degree of damage caused by the herbicide was measured for each plant according to the plant growth status 3 days after spraying (3 DAT), 7 days after spraying (7 DAT), 14 days after spraying (14 DAT) and 21 days after spraying (21 DAT): a growth status equivalent to that of the untreated plants is defined as having a damage degree of 0%; the case where leaves are partially chlorotic and yellow but the normal plant growth is substantially not affected is defined as having a damage degree of 50%; and the case where the whole plant is purple and dying is defined as having a damage degree of 100%. The maize plants into which the SUM1-02 nucleotide sequence was introduced were of two strains in total (S7 and S8), the maize plants into which the control sequence 1 was introduced were of two strains in total (S9 and S10), the maize plants into which the control sequence 2 was introduced were of two strains in total (S11 and S12) and the wild-type maize plants were of one strain in total (CK2); and 10-15 plants were selected from each strain and tested. The results are as shown in Table 3.

TABLE 3

Experimental results of the herbicide tolerance of transgenic maize T1 plants

| Treatment | Maize genotypes | Average damage % 3DAT | Average damage % 7DAT | Average damage % 14DAT | Average damage % 21DAT |
|---|---|---|---|---|---|
| Blank solvent (water) | S7 | 0 | 0 | 0 | 0 |
| | S8 | 0 | 0 | 0 | 0 |
| | S9 | 0 | 0 | 0 | 0 |
| | S10 | 0 | 0 | 0 | 0 |
| | S11 | 0 | 0 | 0 | 0 |
| | S12 | 0 | 0 | 0 | 0 |
| | CK2 | 0 | 0 | 0 | 0 |

TABLE 3-continued

Experimental results of the herbicide tolerance of transgenic maize T1 plants

| Treatment | Maize genotypes | Average damage % 3DAT | Average damage % 7DAT | Average damage % 14DAT | Average damage % 21DAT |
|---|---|---|---|---|---|
| 72 g ai/ha | S7 | 0 | 0 | 0 | 0 |
| tribenuron- | S8 | 0 | 0 | 0 | 0 |
| methyl | S9 | 14 | 18 | 15 | 14 |
| (4xTri.) | S10 | 15 | 19 | 16 | 14 |
| | S11 | 16 | 19 | 16 | 14 |
| | S12 | 15 | 18 | 15 | 13 |
| | CK2 | 41 | 88 | 100 | 100 |
| 120 g ai/ha | S7 | 8 | 0 | 0 | 0 |
| sulfometuron- | S8 | 5 | 0 | 0 | 0 |
| methyl | S9 | 16 | 20 | 16 | 13 |
| (4xSul.) | S10 | 17 | 21 | 17 | 14 |
| | S11 | 15 | 19 | 16 | 14 |
| | S12 | 16 | 20 | 17 | 15 |
| | CK2 | 48 | 83 | 100 | 100 |
| 136 g ai/ha | S7 | 0 | 0 | 0 | 0 |
| halosulfuron- | S8 | 0 | 0 | 0 | 0 |
| methyl | S9 | 8 | 10 | 16 | 18 |
| (4xHal.) | S10 | 9 | 15 | 17 | 20 |
| | S11 | 6 | 16 | 16 | 18 |
| | S12 | 7 | 17 | 15 | 19 |
| | CK2 | 10 | 20 | 21 | 19 |
| 100 g ai/ha | S7 | 6 | 15 | 12 | 10 |
| pyrazosulfuron- | S8 | 4 | 13 | 15 | 11 |
| ethyl | S9 | 28 | 34 | 28 | 25 |
| (4xPyr.) | S10 | 26 | 40 | 30 | 24 |
| | S11 | 27 | 39 | 30 | 24 |
| | S12 | 28 | 39 | 29 | 23 |
| | CK2 | 38 | 79 | 100 | 100 |
| 120 g ai/ha | S7 | 0 | 0 | 0 | 0 |
| thifensulfuron | S8 | 0 | 0 | 0 | 0 |
| (4xThi.) | S9 | 4 | 6 | 17 | 18 |
| | S10 | 3 | 5 | 16 | 21 |
| | S11 | 2 | 4 | 16 | 20 |
| | S12 | 3 | 3 | 15 | 19 |
| | CK2 | 14 | 33 | 44 | 50 |
| 120 g ai/ha | S7 | 0 | 0 | 0 | 0 |
| bensulfuron- | S8 | 0 | 0 | 0 | 0 |
| methy | S9 | 16 | 10 | 6 | 12 |
| (4xBen.) | S10 | 15 | 11 | 5 | 12 |
| | S11 | 15 | 10 | 5 | 12 |
| | S12 | 16 | 11 | 6 | 13 |
| | CK2 | 40 | 83 | 100 | 100 |
| 30 g ai/ha | S7 | 2 | 0 | 0 | 0 |
| metsulfuron- | S8 | 3 | 0 | 0 | 0 |
| methyl | S9 | 14 | 10 | 18 | 14 |
| (4xMet.) | S10 | 15 | 12 | 19 | 15 |
| | S11 | 16 | 12 | 18 | 14 |
| | S12 | 15 | 11 | 18 | 13 |
| | CK2 | 40 | 86 | 100 | 100 |
| 60 g ai/ha | S7 | 0 | 0 | 0 | 0 |
| ethametsulfuron- | S8 | 0 | 0 | 0 | 0 |
| methyl | S9 | 13 | 19 | 16 | 14 |
| (4xEth.) | S10 | 14 | 10 | 16 | 13 |
| | S11 | 14 | 10 | 15 | 13 |
| | S12 | 13 | 10 | 15 | 12 |
| | CK2 | 45 | 81 | 100 | 100 |

TABLE 3-continued

Experimental results of the herbicide tolerance of transgenic maize T1 plants

| Treatment | Maize genotypes | Average damage % 3DAT | Average damage % 7DAT | Average damage % 14DAT | Average damage % 21DAT |
|---|---|---|---|---|---|
| 60 g ai/ha | S7 | 2 | 0 | 0 | 0 |
| chlorimuron- | S8 | 3 | 0 | 0 | 0 |
| ethyl | S9 | 15 | 12 | 19 | 14 |
| (4xChl.) | S10 | 16 | 13 | 20 | 15 |
| | S11 | 16 | 12 | 19 | 14 |
| | S12 | 15 | 12 | 20 | 15 |
| | CK2 | 43 | 88 | 100 | 100 |

For the maize, four-fold field concentration of most sulfonylurea herbicides is an effective dose distinguishing sensitive plants from plants having an average level of resistance. The results in Table 3 showed that the herbicide tolerant protein SUM1 imparted transgenic maize plants with the sulfonylurea herbicide tolerance; and for any of the sulfonylurea herbicides, compared with the maize plants into which the control sequence 1 was introduced and the maize plants into which the control sequence 2 was introduced, the maize plants into which the SUM1-02 nucleotide sequence was introduced had a significantly increased tolerance to sulfonylurea herbicides; while wild-type maize plants had no tolerance to most sulfonylurea herbicides.

In conclusion, the herbicide tolerant protein SUM1 of the present invention can exhibit a higher tolerance to sulfonylurea herbicides, and the SUM1-01 nucleotide sequence and SUM1-02 nucleotide sequence containing the herbicide tolerant protein SUM1 coding sequences, are particularly suitable for expression in plants due to the use of the preferred codons of plants. The *Arabidopsis thaliana* plants into which the SUM1-01 nucleotide sequence was introduced, the soybean plants into which the SUM1-01 nucleotide sequence was introduced and the maize plants into which the SUM1-02 nucleotide sequence was introduced all have a strong tolerance to sulfonylurea herbicides and can tolerate four-fold field concentrations, and therefore, the herbicide tolerant protein SUM1 has a broad application prospect in plants.

Finally, it should be stated that the above embodiments are merely used for illustrating, rather than limiting, the technical solution of the present invention; and although the present invention has been described in detail with reference to the preferred embodiments, a person skilled in the art should understand that modifications or equivalent substitutions may be made to the technical solution of the present invention without departing from the spirit and scope of the technical solution of the present invention.

The invention claimed is:

1. A herbicide tolerant protein:

consisting of the amino acid sequence as shown in SEQ ID NO: 1.

2. A herbicide tolerant gene, comprising:

consisting of a polynucleotide sequence encoding the herbicide tolerant protein of claim 1.

3. An expression cassette or a recombinant vector, comprising the herbicide tolerant gene of claim 2 under regulation of an operably linked regulatory sequence.

4. A method for producing a herbicide tolerant protein, comprising:

obtaining a cell of a transgenic host organism containing the herbicide tolerant gene of claim 2 or an expression cassette comprising the herbicide tolerant gene;

cultivating the cell of the transgenic host organism under conditions allowing production of the herbicide tolerant protein; and recovering the herbicide tolerant protein.

5. A method for increasing the range of herbicides which can be tolerated, comprising: co-expressing the herbicide tolerant protein of claim 1 with at least one second protein which is different from the herbicide tolerant protein in a plant.

6. A method for selecting transformed plant cells, comprising: transforming a plurality of plant cells with the herbicide tolerant gene of claim 2 or an expression cassette comprising the herbicide tolerant gene, and cultivating the cells under a concentration of a herbicide which allows the growth of the transformed cells expressing the herbicide tolerant gene or the expression cassette, while killing the untransformed cells or inhibiting the growth of the untransformed cells, wherein the herbicide is a sulfonylurea herbicide.

7. A method for controlling weeds, comprising: applying an effective dose of a sulfonylurea herbicide to a field in which a target plant is planted, wherein the plant contains the herbicide tolerant gene of claim 2 or an expression cassette comprising the herbicide tolerant gene.

8. A method for protecting a plant from damage caused by a sulfonylurea herbicide, comprising: introducing the herbicide tolerant gene of claim 2 or an expression cassette comprising the herbicide tolerant gene or a recombinant vector comprising the herbicide tolerant gene into a plant, to make the post-introduction plant produce a sufficient amount of herbicide tolerant protein to protect the plant from being damaged by the sulfonylurea herbicide.

9. A method for controlling glyphosate resistant weeds in a field of a glyphosate tolerant plant, comprising: applying an effective dose of a sulfonylurea herbicide to a field in which the glyphosate tolerant plant is planted, wherein the glyphosate tolerant plant contains the herbicide tolerant gene of claim 2 or an expression cassette comprising the herbicide tolerant gene.

10. A method for imparting sulfonylurea herbicide tolerance to a plant, comprising: introducing the herbicide tolerant gene of claim 2 or an expression cassette comprising the herbicide tolerant gene or a recombinant vector comprising the herbicide tolerant gene.

11. A method for producing a plant which is tolerant to a sulfonylurea herbicide, comprising: introducing the herbicide tolerant gene of claim 2 or an expression cassette comprising the herbicide tolerant gene or a recombinant vector comprising the herbicide tolerant gene into the genome of the plant.

12. A method for cultivating a plant which is tolerant to a sulfonylurea herbicide, comprising:

planting at least one plant propagule, the genome of which contains the herbicide tolerant gene of claim 2 or an expression cassette comprising the herbicide tolerant gene;

allowing the plant propagule to grow into a plant; and applying an effective dose of the sulfonylurea herbicide to a plant growing environment comprising at least the plant, and harvesting the plant having a reduced plant damage and/or an increased plant yield compared to other plant without the herbicide tolerant gene or the expression cassette.

13. A planting system for controlling weed growth, comprising: a sulfonylurea herbicide and a plant growing environment in which at least one target plant exists, wherein the plant contains the herbicide tolerant gene of claim 2 or an expression cassette comprising the herbicide tolerant gene.

14. A planting system for controlling glyphosate resistant weeds in a field of a glyphosate tolerant plant, comprising: a sulfonylurea herbicide, a glyphosate herbicide and a field in which at least one target plant is planted, wherein the glyphosate tolerant plant contains the herbicide tolerant gene of claim 2 or an expression cassette comprising the herbicide tolerant gene.

15. The method according to claim 4, wherein the transgenic host organism comprises plants, animals, bacteria, yeasts, baculoviruses, nematodes, or algae.

16. The method according to claim 5, wherein the second protein is 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome-like proteins and/or protoporphyrinogen oxidase.

17. The method according to claim 7, wherein the plant is a monocotyledonous plant or a dicotyledonous plant.

18. The method according to claim 17, wherein the plant is maize, soybean, *Arabidopsis thaliana*, cotton, rape, rice, sorghum, wheat, barley, millet, sugar cane or oats.

19. The method according to claim 7, wherein the sulfonylurea herbicide is tribenuron-methyl, sulfometuron-methyl, halosulfuron-methyl, pyrazosulfuron-ethyl, thifensulfuron-methyl, bensulfuron-methyl, metsulfuron-methyl, ethametsulfuron-methyl or chlorimuron-ethyl.

20. The herbicide tolerant gene of claim 2, wherein the polynucleotide sequence consists of the sequence of SEQ ID NO: 2 or SEQ ID NO: 3.

* * * * *

SEQUENCE LISTING

```
<160> NUMBER OF SEQ ID NOS: 22

<210> SEQ ID NO 1
<211> LENGTH: 350
<212> TYPE: PRT
<213> ORGANISM: Artificial Sequence
<220> FEATURE:
<223> OTHER INFORMATION: SUM1 Amino acid sequence
```

-continued

<400> SEQUENCE: 1

```
Met Ser Lys Arg Lys Val Val Leu Ala Glu Gln Gly Ser Phe Tyr Ile
1               5                   10                  15

Gly Gly Arg Thr Val Thr Gly Pro Gly Lys Phe Asp Pro Ser Lys Pro
            20                  25                  30

Val Ile Pro Tyr Ser Asn Glu Gly Ala Thr Phe Tyr Ile Asn Gln Met
        35                  40                  45

Tyr Val Asn Phe Gln Ala Pro Val Arg Pro Arg Gly Leu Pro Leu Val
    50                  55                  60

Phe Trp His Gly Gly Gly Leu Thr Gly His Ile Trp Glu Ser Thr Pro
65                  70                  75                  80

Asp Gly Arg Pro Gly Phe Gln Thr Leu Phe Val Gln Asp Arg His Thr
                85                  90                  95

Val Tyr Thr Ile Asp Gln Pro Gly Arg Gly Arg Gly Asn Ile Pro Thr
            100                 105                 110

Phe Asn Gly Pro Phe Gly Gln Leu Glu Glu Glu Ser Ile Val Asn Thr
        115                 120                 125

Val Thr Gly Asn Ser Ser Lys Glu Gly Ala Trp Val Arg Asp Arg Leu
    130                 135                 140

Gly Pro Ala Pro Gly Gln Phe Phe Glu Asn Ser Gln Phe Pro Arg Gly
145                 150                 155                 160

Tyr Glu Asp Asn Tyr Phe Lys Glu Met Gly Phe Ser Pro Ser Ile Ser
                165                 170                 175

Ser Asp Glu Ile Val Asp Ala Val Val Lys Leu Val Thr His Ile Gly
            180                 185                 190

Pro Cys Val Leu Val Thr His Ser Ala Ser Gly Val Leu Gly Met Arg
        195                 200                 205

Val Ala Thr His Ala Lys Asn Val Arg Gly Ile Val Ala Tyr Glu Pro
    210                 215                 220

Ala Thr Ser Ile Phe Pro Lys Gly Lys Val Pro Glu Ile Pro Pro Leu
225                 230                 235                 240

Ala Asp Lys Lys Ser Gln Ile Phe Pro Pro Phe Glu Ile Gln Glu Ser
                245                 250                 255

Tyr Phe Lys Lys Leu Ala Lys Ile Pro Ile Gln Phe Val Phe Gly Asp
            260                 265                 270

Asn Ile Pro Lys Asn Pro Lys Ser Ala Tyr Trp Phe Leu Asp Trp Trp
        275                 280                 285

Arg Val Thr Arg Tyr Ala His Ser Leu Ser Leu Glu Ala Ile Asn Lys
    290                 295                 300

Leu Gly Gly Gln Ala Ser Leu Leu Asp Leu Pro Thr Ala Gly Leu Arg
305                 310                 315                 320

Gly Asn Thr His Phe Pro Phe Thr Asp Arg Asn Asn Val Gln Val Ala
                325                 330                 335

Ser Leu Leu Ser Asp Phe Leu Gly Lys His Gly Leu Asp Gln
            340                 345                 350
```

<210> SEQ ID NO 2
<211> LENGTH: 1053
<212> TYPE: DNA
<213> ORGANISM: Artificial Sequence
<220> FEATURE:
<223> OTHER INFORMATION: SUM1-01 Nucleotide sequence -continued

<400> SEQUENCE: 2

```
atgtctaaga gaaaggtggt gctggctgaa caagggtcat tttacatagg gggtaggact     60
gttactggtc ctggcaagtt tgatccatcc aaacctgtga taccctacag taacgaagga    120
gcaacattct atattaacca aatgtatgtt aacttccagg ccccagtgag acctagggga    180
cttccattgg ttttctggca tggaggtggc ttgactggtc acatctggga gtctacacct    240
gacggcagac ccgggtttca aaccctcttc gttcaggata ggcataccgt gtacactatt    300
gaccaacctg ggagaggaag ggtaacatc ccaactttta acggaccttt cggacagttg     360
gaggaagaga gtattgttaa cactgtgaca ggaaattctt caaaggaagg tgcctgggtg    420
agagataggc ttggccctgc tcccgggcaa tttttcgaga actctcagtt tcctagaggc    480
tatgaagaca attactttaa ggagatggga ttcagcccat ctatatccag tgatgaaatt    540
gttgacgctg ttgtgaaact cgtgacccat attggtcctt gtgttctggt gactcactca    600
gcatccggcg ttcttgggat gagagtggct acacacgcaa agaatgttag gggaattgtg    660
gcctatgaac cagctacctc aatcttcccc aagggaaaag ttccagagat accacctctc    720
gctgataaga aaagccaaat ctttcccca ttcgaaatac aggagtctta ctttaagaaa     780
cttgccaaga ttccaatcca atttgttttc ggagataaca tccccaagaa tccaaaatca    840
gcatattggt tcctggactg gtggagagtg acaagatacg cacatagtct cagcctggag    900
gccataaaca aattgggggg acaagcttcc cttttggatc ttcctactgc aggattgaga    960
ggtaatacac actttccctt caccgatagg aacaatgttc aggtggcttc tctcctgtca   1020
gactttctgg gtaaacacgg tctggatcaa tga                                1053
```

<210> SEQ ID NO 3
<211> LENGTH: 1053
<212> TYPE: DNA
<213> ORGANISM: Artificial Sequence
<220> FEATURE:
<223> OTHER INFORMATION: SUM1-02 Nucleotide sequence

<400> SEQUENCE: 3

```
atgagcaaga ggaaggtggt tctggctgag caggggtcgt tctacattgg ggggcggact     60
gtgaccgggc ccggcaagtt cgacccatcg aagcctgtca ttccgtactc taacgagggc    120
gctacgttct acatcaacca gatgtacgtg aatttccagg ctcccgtccg cccaaggggc    180
ctcccactgg tgttctggca cggcgggggc ctgacaggcc atatctggga gtccactcca    240
gatggccgcc cagggttcca gacactcttc gttcaggaca ggcacacagt gtacactatt    300
gatcagccag ggaggggcag gggaacatc cctaccttca atggcccatt cgggcagctg     360
gaggaggagt ccatcgtgaa caccgtcacg ggcaattcca gcaaggaggg ggcttgggtc    420
agggaccggc tcggcccggc cccagggcag ttcttcgaga actctcagtt cccccggggc    480
tacgaggata attacttcaa ggagatgggc ttctcaccat ccatctcgtc tgacgagatt    540
gtcgatgccg tggtcaagct cgttacccac atcggccctt gcgttctggt gacgcatagc    600
gcttcgggcg tcctcgggat gagggttgct acacatgcga agaacgttcg cggcatcgtg    660
gcttacgagc cggccacttc cattttcccc aagggcaagg tgccagagat cccaccactg    720
gccgacaaga agtcacagat cttcccacct ttcgagattc aggagtccta cttcaagaag    780
ctcgctaaga tccccattca gttcgtgttc ggcgacaaca ttcctaagaa tccgaagagc    840
gcgtactggt tcctggattg gtggcgcgtc acgcgctacg cgcactctct ctcactggag    900
gctatcaaca agctcggggg ccaggcctcg ctcctggacc tccctaccgc tggcctgagg    960
```

-continued gggaacaccc atttcccgtt cacggatcgg aacaatgtcc aggttgcgtc cctcctgagc 1020
gatttcctcg gcaagcacgg gctggatcag tga 1053

<210> SEQ ID NO 4
<211> LENGTH: 1322
<212> TYPE: DNA
<213> ORGANISM: Arabidopsis thaliana

<400> SEQUENCE: 4
gtcgacctgc aggtcaacgg atcaggatat tcttgtttaa gatgttgaac tctatggagg 60
tttgtatgaa ctgatgatct aggaccggat aagttccctt cttcatagcg aacttattca 120
aagaatgttt tgtgtatcat tcttgttaca ttgttattaa tgaaaaaata ttattggtca 180
ttggactgaa cacgagtgtt aaatatggac caggccccaa ataagatcca ttgatatatg 240
aattaaataa caagaataaa tcgagtcacc aaaccacttg cctttttta cgagacttgt 300 tcaccaactt gatacaaaag tcattatcct atgcaaatca ataatcatac aaaaatatcc 360
aataacacta aaaaattaaa agaaatggat aatttcacaa tatgttatac gataaagaag 420
ttacttttcc aagaaattca ctgattttat aagcccactt gcattagata aatggcaaaa 480
aaaaacaaaa aggaaaagaa ataaagcacg aagaattcta gaaaatacga aatacgcttc 540
aatgcagtgg gacccacggt tcaattattg ccaattttca gctccaccgt atatttaaaa 600
aataaaacga taatgctaaa aaaatataaa tcgtaacgat cgttaaatct caacggctgg 660
atcttatgac gaccgttaga aattgtggtt gtcgacgagt cagtaataaa cggcgtcaaa 720
gtggttgcag ccggcacaca cgagtcgtgt ttatcaactc aaagcacaaa tacttttcct 780
caacctaaaa ataaggcaat tagccaaaaa caactttgcg tgtaaacaac gctcaataca 840
cgtgtcattt tattattagc tattgcttca ccgccttagc tttctcgtga cctagtcgtc 900
ctcgtctttt cttcttcttc ttctataaaa caatacccaa agcttcttct tcacaattca 960
gatttcaatt tctcaaaatc ttaaaaactt tctctcaatt ctctctaccg tgatcaaggt 1020
aaatttctgt gttccttatt ctctcaaaat cttcgatttt gttttcgttc gatcccaatt 1080
tcgtatatgt tctttggttt agattctgtt aatcttagat cgaagacgat tttctgggtt 1140
tgatcgttag atatcatctt aattctcgat tagggtttca taaatatcat ccgatttgtt 1200
caaataattt gagttttgtc gaataattac tcttcgattt gtgatttcta tctagatctg 1260
gtgttagttt ctagtttgtg cgatcgaatt tgtcgattaa tctgagtttt tctgattaac 1320
ag 1322

<210> SEQ ID NO 5
<211> LENGTH: 253
<212> TYPE: DNA
<213> ORGANISM: Agrobacterium tumefaciens

<400> SEQUENCE: 5
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

-continued

<210> SEQ ID NO 6
<211> LENGTH: 530
<212> TYPE: DNA
<213> ORGANISM: Cauliflower mosaic virus

<400> SEQUENCE: 6
ccatggagtc aaagattcaa atagaggacc taacagaact cgccgtaaag actggcgaac 60
agttcataca gagtctctta cgactcaatg acaagaagaa aatcttcgtc aacatggtgg 120
agcacgacac gcttgtctac tccaaaaata tcaaagatac agtctcagaa gaccaaaggg 180
caattgagac ttttcaacaa agggtaatat ccggaaacct cctcggattc cattgcccag 240
ctatctgtca ctttattgtg aagatagtgg aaaaggaagg tggctcctac aaatgccatc 300
attgcgataa aggaaaggcc atcgttgaag atgcctctgc cgacagtggt cccaaagatg 360
gacccccacc cacgaggagc atcgtggaaa aagaagacgt tccaaccacg tcttcaaagc 420
aagtggattg atgtgatatc tccactgacg taagggatga cgcacaatcc cactatcctt 480
cgcaagaccc ttcctctata taaggaagtt catttcattt ggagaggaca 530

<210> SEQ ID NO 7
<211> LENGTH: 552
<212> TYPE: DNA
<213> ORGANISM: Streptomyces viridochromogenes

<400> SEQUENCE: 7
atgtctccgg agaggagacc agttgagatt aggccagcta cagcagctga tatggccgcg 60
gtttgtgata tcgttaacca ttacattgag acgtctacag tgaactttag gacagagcca 120
caaacaccac aagagtggat tgatgatcta gagaggttgc aagatagata cccttggttg 180
gttgctgagg ttgagggtgt tgtggctggt attgcttacg ctgggccctg gaaggctagg 240
aacgcttacg attggacagt tgagagtact gtttacgtgt cacataggca tcaaaggttg 300
ggcctaggat ccacattgta cacacatttg cttaagtcta tggaggcgca aggttttaag 360
tctgtggttg ctgttatagg ccttccaaac gatccatctg ttaggttgca tgaggctttg 420
ggatacacag cccggggtac attgcgcgca gctggataca agcatggtgg atggcatgat 480
gttggttttt ggcaaaggga ttttgagttg ccagctcctc caaggccagt taggccagtt 540
acccagatct ga 552

<210> SEQ ID NO 8
<211> LENGTH: 195
<212> TYPE: DNA
<213> ORGANISM: Cauliflower mosaic virus

<400> SEQUENCE: 8
ctgaaatcac cagtctctct ctacaaatct atctctctct ataataatgt gtgagtagtt 60
cccagataag ggaattaggg ttcttatagg gtttcgctca tgtgttgagc atataagaaa 120
cccttagtat gtatttgtat ttgtaaaata cttctatcaa taaaatttct aattcctaaa 180
accaaaatcc agtgg 195

<210> SEQ ID NO 9
<211> LENGTH: 1197
<212> TYPE: DNA
<213> ORGANISM: Artificial Sequence
<220> FEATURE:
<223> OTHER INFORMATION: Control sequence 1

<400> SEQUENCE: 9
atggaaaccg ataaaaaaac cggaacgtcc cgcagatcat ttgtgaaggc tgctggaacc 60
ggcgcaatag gaatagcgac gctgccgctt tcgactgcaa ctgctttcgc ggaaactgac 120
aacgtggagc ttgcccaatc gaagcggaag gttgtccttg ctgaacaagg cagtttctac 180
atcgggggca gaacagtaac cgggcctgga aaattcgatc cgtcaaagcc ggtaattcca 240
tattccaacg aaggtgccac gttttatatc aatcaaatgt acgtaaactt tcaagctcct 300
gtgcgccctc gtgggctgcc tctagtcttt tggcatgggg gcggactaac cggccatatc 360
tgggaatcta ccccagacgg ccgcccccgga tttcagaccc tctttgttca agatcggcat 420
acggtctaca cgattgatca gccagggcgc ggaaggggca atattcctac ctttaatggc 480
ccttttgggc agttggaaga agagtcgatt gttaacactg ttaccggaaa ctccagtaaa 540
gaaggagcgt gggttagaga tcgactaggg cccgctcccg gccagttttt tgagaacagc 600
caattcccac gtggttatga agacaactac ttcaaggaga tggggttcag tccgtcgatc 660
tcatcagatg agatagtcga cgctgttgtt aaactagtaa ctcacatagg tccttgtgtt 720
ctggtgaccc attcggcttc cggagtactg ggcatgcgag tcgcgacaca cgccaagaac 780
gtgaggggga tcgttgctta tgagcctgcg acaagtatct ttcccaaagg aaaagtgcct 840
gagataccgc ctctcgccga taaaaagtcg caaattttcc cgccgttcga gatccaggag 900
tcttacttta agaagctcgc gaagataccc attcagtttg tcttcggaga taatatcccc 960
aagaacccta aatccgccta ttggttcttg gactggtgga gagtcactcg ctacgctcac 1020
agcttgtcac tcgaggctat caataagctc ggtggtcaag cgtctctttt ggatttgccg 1080
actgcgggac ttcgcggcaa cacgcatttt ccattcaccg accggaataa cgtgcaggtc 1140
gcttctctgt tatctgattt cctcggaaag cacggcttag atcagaacga aagctga 1197

<210> SEQ ID NO 10
<211> LENGTH: 1089
<212> TYPE: DNA
<213> ORGANISM: Artificial Sequence
<220> FEATURE:
<223> OTHER INFORMATION: Control sequence 2

<400> SEQUENCE: 10
atggaaactg acaacgtgga gcttgcccaa tcgaagcgga aggttgtcct tgctgaacaa 60
ggcagtttct acatcggggg cagaacagta accgggcctg gaaaattcga tccgtcaaag 120
ccggtaattc catattccaa cgaaggtgcc acgttttata tcaatcaaat gtacgtaaac 180
tttcaagctc ctgtgcgccc tcgtgggctg cctctagtct tttggcatgg gggcggacta 240
accggccata tctgggaatc taccccagac ggccgccccg gatttcagac cctctttgtt 300
caagatcggc atacggtcta cacgattgat cagccagggc gcggaagggg caatattcct 360
acctttaatg gcccttttgg gcagttggaa gaagagtcga ttgttaacac tgttaccgga 420
aactccagta aagaaggagc gtgggttaga gatcgactag ggcccgctcc cggccagttt 480
tttgagaaca gccaattccc acgtggttat gaagacaact acttcaagga gatggggttc 540
agtccgtcga tctcatcaga tgagatagtc gacgctgttg ttaaactagt aactcacata 600
ggtccttgtg ttctggtgac ccattcggct tccggagtac tgggcatgcg agtcgcgaca 660
cacgccaaga acgtgagggg gatcgttgct tatgagcctg cgacaagtat ctttcccaaa 720
ggaaaagtgc ctgagatacc gcctctcgcc gataaaaagt cgcaaatttt cccgccgttc 780

-continued

```
gagatccagg agtcttactt taagaagctc gcgaagatac ccattcagtt tgtcttcgga    840

gataatatcc ccaagaaccc taaatccgcc tattggttct tggactggtg gagagtcact    900

cgctacgctc acagcttgtc actcgaggct atcaataagc tcggtggtca agcgtctctt    960

ttggatttgc cgactgcggg acttcgcggc aacacgcatt ttccattcac cgaccggaat   1020

aacgtgcagg tcgcttctct gttatctgat ttcctcggaa agcacggctt agatcagaac   1080

gaaagctga                                                           1089
```

<210> SEQ ID NO 11
<211> LENGTH: 1534
<212> TYPE: DNA
<213> ORGANISM: Brassica napus

<400> SEQUENCE: 11

```
gattatgaca ttgctcgtgg aatgggacag ttatggtatt tttttgtaat aaattgtttc     60

cattgtcatg agattttgag gttaatctat gagacattga atcacttagc attagggatt    120

aagtagtcac aaatcgcatt caagaagctg aagaacacgt tatggtctaa tggttgtgtc    180

tctttattag aaaatgttgg tcagtagcta tatgcactgt ttctgtaaaa ccatgttggt    240

gttgtgttta tttcaagaca catgttgagt ccgttgattc agagcttttg tcttcgaaca    300

caatctagag agcaaatttg ggttcaattt ggatatcaat atgggttcga ttcagataga    360

acaataccct ttgatgtcgg gtttcgattt ggttgagatt catttttatc gggtttggtt    420

cgattttcga attcggttta ttcgccccct catagcatct acattctgca gattaatgta    480

caagttatgg aaaaaaaaat gtggttttcg aattcggttt agtagctaaa cgttgcttgc    540

agtgtagtta tgggaattat gaaacacgac cgaaggtatc aattagaaga acgggtcaac    600

gggtaagtat tgagaaatta ccggagggta aaaataaaca gtattctttt tttttcttaa    660

cgaccgacca aggttaaaaa aagaaaggag gacgagatac aggggcatga ctgtaattgt    720

acataagatc tgatctttaa accctaggtt tccttcgcat cagcaactat aaataattct    780

gagtgccact cttcttcatt cctagatctt tcgccttatc gctttagctg aggtaagcct    840

ttctatacgc atagacgctc tcttttctct tctctcgatc ttcgttgaaa cggtcctcga    900

tacgcatagg atcggttaga atcgttaatc tatcgtctta gatcttcttg attgttgaat    960

tgagcttcta ggatgtattg tatcatgtga tggatagttg attggatctc tttgagtgaa   1020

ctagctagct ttcgatgcgt gtgatttcag tataacagga tccgatgaat tatagctcgc   1080

ttacaattaa tctctgcaga tttattgttt aatcttggat ttgatgctcg ttgttgatag   1140

aggatcgttt atagaactta ttgattctgg aattgagctt gtgtgatgta ttgtatcatg   1200

tgatcgatag ctgatggatc tatttgagtg aactagcgta cgatcttaag atgagtgtgt   1260

attgtgaact gatgattcga gatcagcaaa acaagatctg atgatatctt cgtcttgtat   1320

gcatcttgaa tttcatgatt ttttattaat tatagctcgc ttagctcaaa ggatagagca   1380

ccacaaaatt ttattgtggt agaaatcggt tcgattccga tagcagctta ctgtgatgaa   1440

tgattttgag atttggtatt tgatatatgt ctactgtgtt gaatgatcgt ttatgcattg   1500

tttaatcgct gcagatttgc attgacaagt agcc                               1534
```

<210> SEQ ID NO 12
<211> LENGTH: 228
<212> TYPE: DNA
<213> ORGANISM: Arabidopsis thaliana -continued

<400> SEQUENCE: 12
atggcgcaag ttagcagaat ctgcaatggt gtgcagaacc catctcttat ctccaatctc 60
tcgaaatcca gtcaacgcaa atctccctta tcggtttctc tgaagacgca gcagcatcca 120
cgagcttatc cgatttcgtc gtcgtgggga ttgaagaaga gtgggatgac gttaattggc 180
tctgagcttc gtcctcttaa ggtcatgtct tctgtttcca cggcgtgc 228

<210> SEQ ID NO 13
<211> LENGTH: 1368
<212> TYPE: DNA
<213> ORGANISM: Artificial Sequence
<220> FEATURE:
<223> OTHER INFORMATION: EPSPS Gene

<400> SEQUENCE: 13
atgcttcacg gtgcaagcag ccggcccgca accgcccgca aatcctctgg cctttccgga 60
accgtccgca ttcccggcga caagtcgatc tcccaccggt ccttcatgtt cggcggtctc 120
gcgagcggtg aaacgcgcat caccggcctt ctggaaggcg aggacgtcat caatacgggc 180
aaggccatgc aggcgatggg cgcccgcatc cgtaaggaag gcgacacctg gatcatcgat 240
ggcgtcggca atggcggcct cctggcgcct gaggcgccgc tcgatttcgg caatgccgcc 300
acgggctgcc gcctgacgat gggcctcgtc ggggtctacg atttcgacag caccttcatc 360
ggcgacgcct cgctcacaaa gcgcccgatg ggccgcgtgt tgaacccgct gcgcgaaatg 420
ggcgtgcagg tgaaatcgga agacggtgac cgtcttcccg ttaccttgcg cgggccgaag 480
acgccgacgc cgatcaccta ccgcgtgccg atggcctccg cacaggtgaa gtccgccgtg 540
ctgctcgccg gcctcaacac gcccggcatc acgacggtca tcgagccgat catgacgcgc 600
gatcatacgg aaaagatgct gcagggcttt ggcgccaacc ttaccgtcga gacggatgcg 660
gacggcgtgc gcaccatccg cctggaaggc cgcggcaagc tcaccggcca agtcatcgac 720
gtgccgggcg acccgtcctc gacggccttc ccgctggttg cggccctgct tgttccgggc 780
tccgacgtca ccatcctcaa cgtgctgatg aaccccaccc gcaccggcct catcctgacg 840
ctgcaggaaa tgggcgccga catcgaagtc atcaacccgc gccttgccgg cggcgaagac 900
gtggcggacc tgcgcgttcg ctcctccacg ctgaagggcg tcacggtgcc ggaagaccgc 960
gcgccttcga tgatcgacga atatccgatt ctcgctgtcg ccgccgcctt cgcggaaggg 1020
gcgaccgtga tgaacggtct ggaagaactc cgcgtcaagg aaagcgaccg cctctcggcc 1080
gtcgccaatg gcctcaagct caatggcgtg gattgcgatg agggcgagac gtcgctcgtc 1140
gtgcgtggcc gccctgacgg caaggggctc ggcaacgcct cgggcgccgc cgtcgccacc 1200
catctcgatc accgcatcgc catgagcttc ctcgtcatgg gcctcgtgtc ggaaaaccct 1260
gtcacggtgg acgatgccac gatgatcgcc acgagcttcc cggagttcat ggacctgatg 1320
gccgggctgg gcgcgaagat cgaactctcc gatacgaagg ctgcctga 1368

<210> SEQ ID NO 14
<211> LENGTH: 643
<212> TYPE: DNA
<213> ORGANISM: Pisum sativum

<400> SEQUENCE: 14
agctttcgtt cgtatcatcg gtttcgacaa cgttcgtcaa gttcaatgca tcagtttcat 60
tgcgcacaca ccagaatcct actgagtttg agtattatgg cattgggaaa actgtttttc 120
ttgtaccatt tgttgtgctt gtaatttact gtgtttttta ttcggttttc gctatcgaac 180

-continued

```
tgtgaaatgg aaatggatgg agaagagtta atgaatgata tggtcctttt gttcattctc    240

aaattaatat tatttgtttt ttctcttatt tgttgtgtgt tgaatttgaa attataagag    300

atatgcaaac attttgtttt gagtaaaaat gtgtcaaatc gtggcctcta atgaccgaag    360

ttaatatgag gagtaaaaca cttgtagttg taccattatg cttattcact aggcaacaaa    420

tatattttca gacctagaaa agctgcaaat gttactgaat acaagtatgt cctcttgtgt    480

tttagacatt tatgaacttt cctttatgta attttccaga atccttgtca gattctaatc    540

attgctttat aattatagtt atactcatgg atttgtagtt gagtatgaaa atattttta     600

atgcatttta tgacttgcca attgattgac aacatgcatc aat                      643
```

<210> SEQ ID NO 15
<211> LENGTH: 25
<212> TYPE: DNA
<213> ORGANISM: Artificial Sequence
<220> FEATURE:
<223> OTHER INFORMATION: Primer 1

<400> SEQUENCE: 15

```
ctggaaggcg aggacgtcat caata                                           25
```

<210> SEQ ID NO 16
<211> LENGTH: 22
<212> TYPE: DNA
<213> ORGANISM: Artificial Sequence
<220> FEATURE:
<223> OTHER INFORMATION: Primer 2

<400> SEQUENCE: 16

```
tggcggcatt gccgaaatcg ag                                              22
```

<210> SEQ ID NO 17
<211> LENGTH: 28
<212> TYPE: DNA
<213> ORGANISM: Artificial Sequence
<220> FEATURE:
<223> OTHER INFORMATION: Probe 1

<400> SEQUENCE: 17

```
atgcaggcga tgggcgcccg catccgta                                        28
```

<210> SEQ ID NO 18
<211> LENGTH: 1992
<212> TYPE: DNA
<213> ORGANISM: Zea mays

<400> SEQUENCE: 18

```
ctgcagtgca gcgtgacccg gtcgtgcccc tctctagaga taatgagcat tgcatgtcta     60

agttataaaa aattaccaca tattttttt gtcacacttg tttgaagtgc agtttatcta     120

tctttataca tatatttaaa ctttactcta cgaataatat aatctatagt actacaataa    180

tatcagtgtt ttagagaatc atataaatga acagttagac atggtctaaa ggacaattga    240

gtattttgac aacaggactc tacagtttta tctttttagt gtgcatgtgt tctccttttt    300

ttttgcaaat agcttcacct atataatact tcatccattt tattagtaca tccatttagg    360

gtttagggtt aatggttttt atagactaat ttttttagta catctatttt attctatttt    420

agcctctaaa ttaagaaaac taaaactcta ttttagtttt tttatttaat aatttagata    480

taaaatagaa taaaataaag tgactaaaaa ttaaacaaat accctttaag aaattaaaaa    540

aactaaggaa acatttttct tgtttcgagt agataatgcc agcctgttaa acgccgtcga    600
```

-continued

```
cgagtctaac ggacaccaac cagcgaacca gcagcgtcgc gtcgggccaa gcgaagcaga    660

cggcacggca tctctgtcgc tgcctctgga cccctctcga gagttccgct ccaccgttgg    720

acttgctccg ctgtcggcat ccagaaattg cgtggcggag cggcagacgt gagccggcac    780

ggcaggcggc ctcctcctcc tctcacggca cggcagctac gggggattcc tttcccaccg    840

ctccttcgct ttcccttcct cgcccgccgt aataaataga caccccctcc acaccctctt    900

tccccaacct cgtgttgttc ggagcgcaca cacacacaac cagatctccc ccaaatccac    960

ccgtcggcac ctccgcttca aggtacgccg ctcgtcctcc cccccccccc ctctctacct   1020

tctctagatc ggcgttccgg tccatggtta gggcccggta gttctacttc tgttcatgtt   1080

tgtgttagat ccgtgtttgt gttagatccg tgctgctagc gttcgtacac ggatgcgacc   1140

tgtacgtcag acacgttctg attgctaact tgccagtgtt tctctttggg gaatcctggg   1200

atggctctag ccgttccgca gacgggatcg atttcatgat ttttttgtt tcgttgcata   1260

gggtttggtt tgccctttc ctttatttca atatatgccg tgcacttgtt tgtcgggtca   1320

tcttttcatg cttttttttg tcttggttgt gatgatgtgg tctggttggg cggtcgttct   1380

agatcggagt agaattctgt ttcaaactac ctggtggatt tattaatttt ggatctgtat   1440

gtgtgtgcca tacatattca tagttacgaa ttgaagatga tggatggaaa tatcgatcta   1500

ggataggtat acatgttgat gcgggtttta ctgatgcata tacagagatg ctttttgttc   1560

gcttggttgt gatgatgtgg tgtggttggg cggtcgttca ttcgttctag atcggagtag   1620

aatactgttt caaactacct ggtgtattta ttaattttgg aactgtatgt gtgtgtcata   1680

catcttcata gttacgagtt taagatggat ggaaatatcg atctaggata ggtatacatg   1740

ttgatgtggg ttttactgat gcatatacat gatggcatat gcagcatcta ttcatatgct   1800

ctaaccttga gtacctatct attataataa acaagtatgt tttataatta ttttgatctt   1860

gatatacttg gatgatggca tatgcagcag ctatatgtgg atttttttag ccctgccttc   1920

atacgctatt tatttgcttg gtactgtttc ttttgtcgat gctcaccctg ttgtttggtg   1980

ttacttctgc ag                                                         1992
```

<210> SEQ ID NO 19
<211> LENGTH: 1176
<212> TYPE: DNA
<213> ORGANISM: Escherichia coli

<400> SEQUENCE: 19

```
atgcaaaaac tcattaactc agtgcaaaac tatgcctggg gcagcaaaac ggcgttgact     60

gaactttatg gtatggaaaa tccgtccagc cagccgatgg ccgagctgtg gatgggcgca    120

catccgaaaa gcagttcacg agtgcagaat gccgccggag atatcgtttc actgcgtgat    180

gtgattgaga gtgataaatc gactctgctc ggagaggccg ttgccaaacg ctttggcgaa    240

ctgcctttcc tgttcaaagt attatgcgca gcacagccac tctccattca ggttcatcca    300

aacaaacaca attctgaaat cggttttgcc aaagaaaatg ccgcaggtat cccgatggat    360

gccgccgagc gtaactataa agatcctaac cacaagccgg agctggtttt tgcgctgacg    420

cctttccttg cgatgaacgc gtttcgtgaa ttttccgaga ttgtctccct actccagccg    480

gtcgcaggtg cacatccggc gattgctcac tttttacaac agcctgatgc cgaacgttta    540

agcgaactgt tcgccagcct gttgaatatg cagggtgaag aaaaatcccg cgcgctggcg    600

attttaaaat cggccctcga tagccagcag ggtgaaccgt ggcaaacgat tcgtttaatt    660

tctgaatttt acccggaaga cagcggtctg ttctccccgc tattgctgaa tgtggtgaaa    720
```

-continued

```
ttgaaccctg gcgaagcgat gttcctgttc gctgaaacac cgcacgctta cctgcaaggc    780

gtggcgctgg aagtgatggc aaactccgat aacgtgctgc gtgcgggtct gacgcctaaa    840

tacattgata ttccggaact ggttgccaat gtgaaattcg aagccaaacc ggctaaccag    900

ttgttgaccc agccggtgaa acaaggtgca gaactggact tcccgattcc agtggatgat    960

tttgccttct cgctgcatga ccttagtgat aaagaaacca ccattagcca gcagagtgcc   1020

gccattttgt tctgcgtcga aggcgatgca acgttgtgga aaggttctca gcagttacag   1080

cttaaaccgg gtgaatcagc gtttattgcc gccaacgaat caccggtgac tgtcaaaggc   1140

cacggccgtt tagcgcgtgt ttacaacaag ctgtaa                             1176


<210> SEQ ID NO 20
<211> LENGTH: 29
<212> TYPE: DNA
<213> ORGANISM: Artificial Sequence
<220> FEATURE:
<223> OTHER INFORMATION: Primer 3

<400> SEQUENCE: 20

gctgtaagag cttactgaaa aaattaaca                                      29


<210> SEQ ID NO 21
<211> LENGTH: 18
<212> TYPE: DNA
<213> ORGANISM: Artificial Sequence
<220> FEATURE:
<223> OTHER INFORMATION: Primer 4

<400> SEQUENCE: 21

cgatctgcag gtcgacgg                                                  18


<210> SEQ ID NO 22
<211> LENGTH: 27
<212> TYPE: DNA
<213> ORGANISM: Artificial Sequence
<220> FEATURE:
<223> OTHER INFORMATION: Probe 2

<400> SEQUENCE: 22

tctcttgcta agctgggagc tcgatcc                                        27
```